United States Patent

Tsuyuki et al.

[11] Patent Number: 6,069,651
[45] Date of Patent: *May 30, 2000

[54] IMAGING APPARATUS FOR ENDOSCOPES

[75] Inventors: Hiroshi Tsuyuki, Hachioji; Akira Hasegawa, Machida; Toshikazu Takayama, Hino; Mitsujiro Konno, Hoya, all of Japan

[73] Assignee: Olympus Optical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/634,982

[22] Filed: Apr. 19, 1996

[30] Foreign Application Priority Data

Apr. 20, 1995 [JP] Japan ................................. 7-094934
Aug. 1, 1995 [JP] Japan ................................. 7-196528
Apr. 12, 1996 [JP] Japan ................................. 8-091013

[51] Int. Cl.$^7$ ................................................. H04N 7/18
[52] U.S. Cl. .......................... 348/75; 348/65; 348/72
[58] Field of Search ................................. 348/65, 66, 72, 348/82, 75; 600/112, 181, 106, 108; H04N 7/18

[56] References Cited

U.S. PATENT DOCUMENTS

| | | | |
|---|---|---|---|
| 4,419,987 | 12/1983 | Ogiu | 600/106 |
| 4,639,772 | 1/1987 | Sluyter et al. | 348/73 |
| 4,905,082 | 2/1990 | Nishigaki et al. | 348/73 |
| 4,926,258 | 5/1990 | Sasaki et al. | 348/72 |
| 5,010,876 | 4/1991 | Henley et al. | 348/65 |
| 5,051,823 | 9/1991 | Copper et al. | 348/66 |
| 5,198,894 | 3/1993 | Hicks | 348/65 |
| 5,245,475 | 9/1993 | Takasugi . | |
| 5,341,240 | 8/1994 | Broome . | |
| 5,396,366 | 3/1995 | Brown . | |
| 5,523,782 | 6/1996 | Williams | 348/66 |
| 5,528,432 | 6/1996 | Donahoo | 359/894 |
| 5,587,736 | 12/1996 | Walls | 348/65 |

FOREIGN PATENT DOCUMENTS 5-80275  10/1992  Japan .
4-289816  4/1993  Japan .

OTHER PUBLICATIONS

Book: Smith, W.J., Modern Optical Engineering, McGraw–Hill, 1990. For Example: pp. 133–158, 1990.

Primary Examiner—Richard Lee
Attorney, Agent, or Firm—Pillsbury Madison & Sutro LLP

[57] ABSTRACT

An imaging apparatus for endoscopes includes an endoscope; a TV camera head incorporating, at least, a solid-state image sensor; and a TV photographic adapter incorporating at least one part of an optical system for forming an image obtained by the endoscope on the solid-state image sensor. At least one of the TV camera head and the TV photographic adapter is hermetically sealed by dampproof members so that autoclaving treatment can be received.

6 Claims, 24 Drawing Sheets

TO OUTPUT AMP.

120

122
121
120
123

FIG. 21A
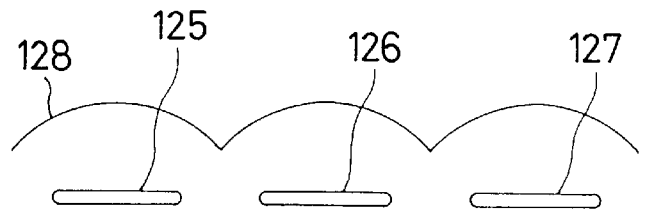
FIG. 21B
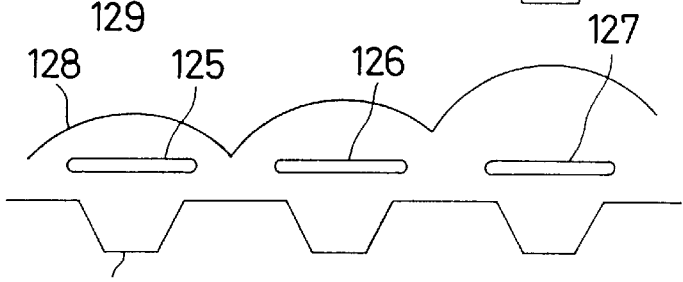
FIG. 21C
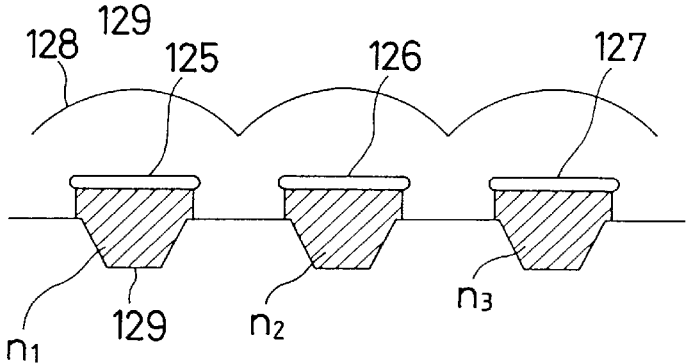
FIG. 22
| | G | G | G | G | G | G |
|---|---|---|---|---|---|---|
| $a_1$ | B | B | R | B | B | R |
| $b_1$ | G | G | G | G | G | G |
| | B | B | R | B | B | R |
| $a_2$ | G | G | G | G | G | G |
| | B | B | R | B | B | R |
LUMINANCE SIGNAL Y=G

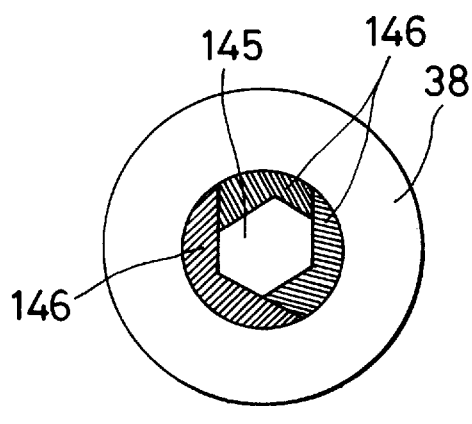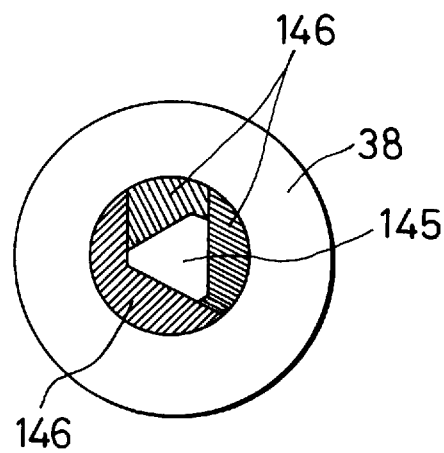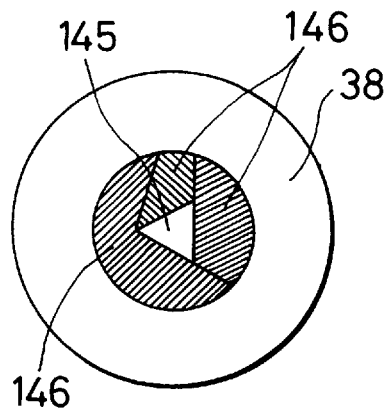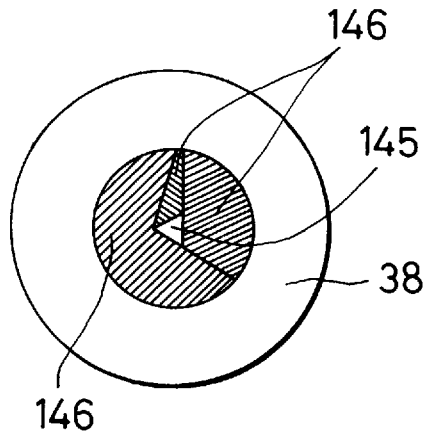

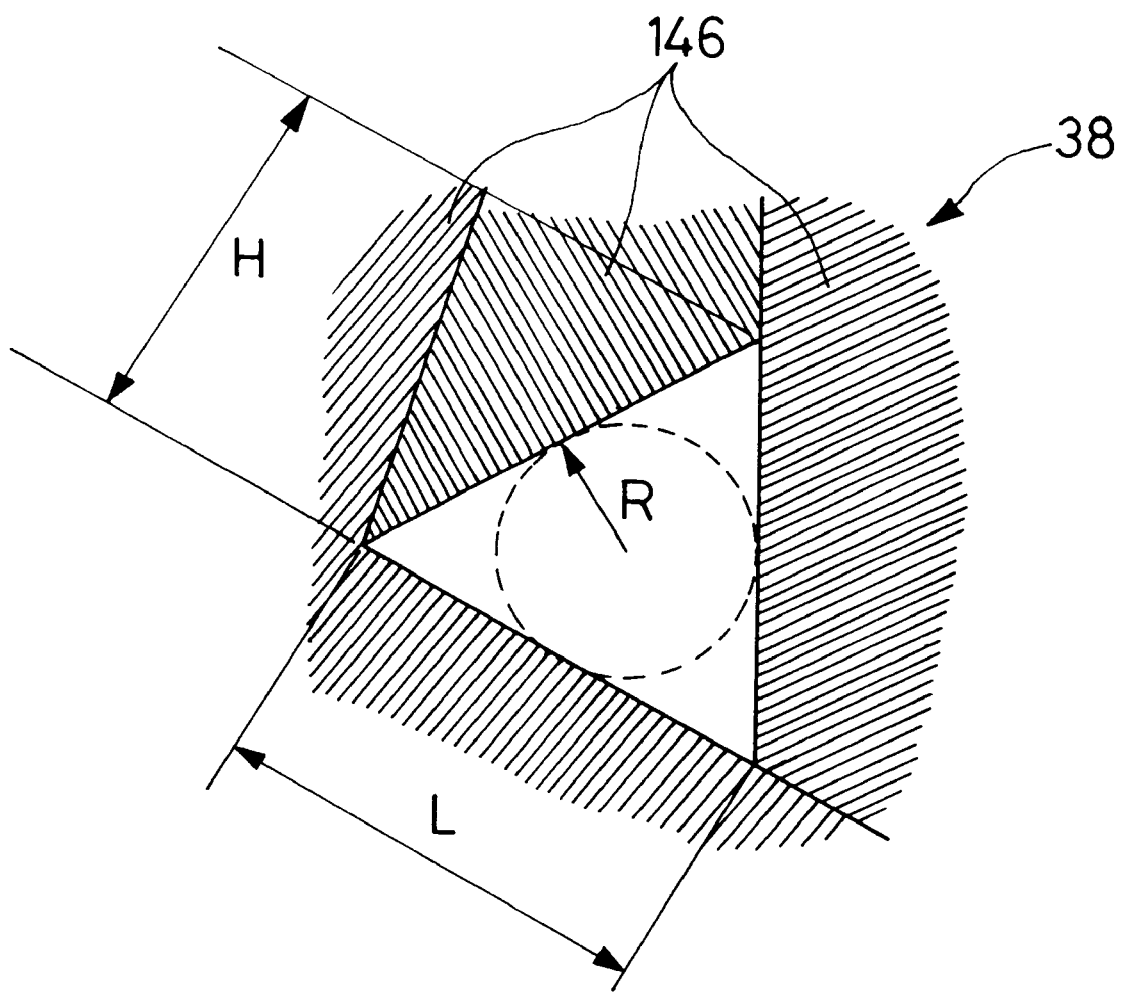

IMAGING APPARATUS FOR ENDOSCOPES

BACKGROUND OF THE INVENTION

1. Field of the Invention

This invention relates to an imaging apparatus for endoscopes in which a TV camera is mounted to the eyepiece section of an endoscope to observe an endoscope image through the TV camera.

2. Description of Related Art

Generally, in order to transmit images, for example, inside a human body, derived from an endoscope to a pickup device, an attachment TV camera is removably mounted at the rear of the eyepiece section of the endoscope. FIG. 1 shows various constructions of an imaging apparatus for endoscopes having such a TV camera attachment. As shown in this figure, conventional imaging apparatuses for endoscopes are roughly divided into the following three combinations according to their applications. In the first case, an endoscope (a rigid endoscope) 1 is connected, through a TV photographic adapter 5 having a focusing function and a TV camera head 7 constructed such that it is separate from the TV photographic adapter 5, to a camera control unit (CCU) 8 so that an image photographed by the TV camera head 7 through the endoscope 1 is displayed on a TV monitor 9. In the second case, the endoscope 1 is connected, such that it is through a TV camera head 13 constructed integral with a TV photographic adapter incorporating an auto-iris device 11, to the CCU 8. In the third case, the endoscope 1 is connected, through an intermediate adapter 14 for focusing and a TV camera head 15 incorporating an imaging optical system 6, to the CCU 8. Here, the endoscope 1 can be used with any one of the TV camera heads 7, 13, or 15 according to its application.

The endoscope 1 comprises an inserting section including an objective lens 2 and a relay lens 3 and an eyepiece section including an eyepiece 4. The objective lens 2 forms an object image Q, which is transmitted to the front of the eyepiece 4 by the relay lens 3 and is re-formed as an image Q'. Light having formed the image Q' emerges from the eyepiece and becomes a nearly parallel light beam. In this way, the object image can be observed through a simple example of eyepiece 4. Also, although the relay lens 3 is drawn in the figure, it is often designed so that image formation is repeated a plural (usually, odd) number of times to transmit the image. The imaging optical system 6, housed in the TV photographic adapter 5 or the TV camera head 13 or 15, receives the light beam leaving the eyepiece 4 of the endoscope 1 and causes the light beam to converge so that the object image Q is formed on a solid-state image sensor 16, such as a CCD, incorporated in the TV camera head 7, 13 or 15.

The TV camera head 13 shown in FIG. 1 is constructed so that when the TV photographic adapter thereof is attached to the eyepiece section of the endoscope 1, the auto-iris device 11 is located at the position where it practically coincides with the exit pupil of the eyepiece 4, and its aperture size can be changed by the driving force of a motor, not shown, provided in the TV photographic adapter. Each of the TV camera heads 7, 13, and 15 is equipped with a filter unit 10 and the CCD 16. An output signal from the CCD 16 is supplied to the CCU 8. The CCU 8 is adapted to convert the output signal into a signal by which the image can be displayed on the TV monitor 9 and to process various signals required. Moreover, the CCU 8 is such that signals for controlling the TV camera and the like are processed when necessary. Reference numeral 12 represents an electric drive path along which a signal for controlling the auto-iris device 11 is transmitted.

When the TV camera head 7 is sterilized, EOG (ethylene oxide gas) and wash water are used, and thus the TV photographic adapter 5 and the TV camera head 7 are designed to have a watertight structure in mutually connecting relation. Specifically, if an O-ring is attached to the connection of either one of the TV photographic adapter 5 and the TV camera head 7, both need not be integrally constructed and can be separated from each other. In this way, various TV photographic adapters can be used as endoscope systems, and hence magnification for observation of an endoscope image which is most suitable for a user's need can be provided. Furthermore, if a focusing ring is used in the TV camera head, it is possible for it to have a focusing function.

In recent years, a sterilization method with a low operating cost has made use of a method of killing all microorganisms by leaving the TV camera head placed, for example, in a high-pressure vapor of 135° C. for five minutes, (i.e., the so-called autoclaving method). This autoclaving method requires that the TV camera head has a fully enclosed structure to prevent water vapor from entering inside the TV camera head. Thus, the TV photographic adapter having the imaging optical system must be constructed such that it is integral with the TV camera head having the CCD so that they are hermetically sealed. Consequently, since a moving part such as a focusing mechanism cannot be provided, it has the problem that the imaging apparatus for endoscopes, including the TV photographic adapter 5 and the TV camera head 7 shown in FIG. 1 cannot be used.

In order to solve this problem, an endoscope imaging apparatus proposed, for example, by Japanese Patent Application No. Hei 6-41395 is available. This apparatus employs the construction including the TV camera head 13 in FIG. 1. The TV camera head 13, instead of having a focusing function, has a variable stop device called the auto-iris to increase the depth of field, and thereby is intended to obviate the out-of-focus defect. Moreover, the apparatus has the merit that the user requires very little focus adjustment.

The prior art imaging apparatus for endoscopes mentioned above is constructed so that the image is formed on the image sensor 16, such as the CCD, in the TV camera head 13 by the imaging optical system 6 disposed behind the eyepiece 4 of the endoscope 1 and can be observed by the monitor 9. This apparatus, however, has the problem of becoming very expensive as a product because the TV camera head 13, although it has autoclaving resistance, has the auto-iris device as well.

Thus, in order to settle this problem, there is an imaging apparatus for endoscopes proposed, for example, by Japanese Patent Application No. Hei 6-22741. This apparatus employs the construction including the TV camera head 15 in FIG. 1. With respect to the TV camera head 15 including the imaging optical system 6 and the CCD 16 and having autoclaving resistance, the apparatus is such that the intermediate adapter 14 for focusing, likewise having autoclaving resistance as a unit, is interposed between the endoscope 1 and the TV camera head 15, and a focusing operation is performed by moving the adapter 14 along the optical axis.

The imaging apparatus for endoscopes constructed as mentioned above, although of autoclaving resistance, can be manufactured at low cost because it has no auto-iris function. However, since the imaging optical system 6 is incorporated in the TV camera head 15, there is the problem that when it is necessary to variously change magnification for observation, the TV camera head 15 must be replaced by another TV camera head having a desired magnification, with a resulting lack of system extension.

In another imaging apparatus for endoscopes of prior art shown in FIG. 2, a TV photographic adapter 25 is removably mounted to the eyepiece section of the endoscope 1 and includes a stop (auto-iris) 31, whose aperture size is variable, and the imaging optical system 6. When the TV photographic adapter 25 is attached to the eyepiece section of the endoscope 1, the stop 31 is located at the position where it practically coincides with the exit pupil of the eyepiece 4, and its aperture size is changed by the driving force of a motor provided in the TV photographic adapter 25. The imaging optical system 6 receives a light beam emerging from the eyepiece 4 and causes the light beam to converge so that when a TV camera head 27 is mounted to the TV photographic adapter 25, the object image is formed on the image sensor 16 such as the CCD. The TV camera head 27 is equipped with the filter unit 10 and the CCD 16. An output signal from the image sensor 16 is supplied to the CCU 8. The CCU 8 is such that the output signal is converted into a signal by which the image can be displayed on the TV monitor 9 and various signals required are processed. Moreover, the CCU 8 is adapted to output signals for controlling the TV camera and the like when necessary. Reference numeral 32 represents electric drive paths along which a signal for controlling the stop 31 is transmitted. Contacts 33 are the connections of the signal lines 32 for controlling the stop 31 and are connected when the TV photographic adapter 25 is attached to the TV camera head 27.

As mentioned above, the conventional apparatus is designed so that the TV photographic adapter 25 having the imaging optical system 6 is mounted behind the eyepiece 4 of the endoscope 1, and the image is formed on the image sensor 16, such as the CCD, in the TV camera head 27 and can be observed by the TV monitor 9 for display.

Also, an outside diameter D of the TV camera head 27 is about 2–3 cm, and a length S where the TV photographic adapter 25 is connected with the TV camera head 27 is a few centimeters.

However, when the image of the endoscope mentioned above is observed by the monitor, there is the problem that the depth of field is small. In recent years, the CCD which is the image sensor of the TV camera has tended toward a high pixel density, which makes a high resolution of an object possible. For this reason, however, since the size of one pixel (pixel pitch) diminishes, an allowable diameter of the circle of confusion must be decreased and the depth of field becomes smaller.

Hence, it is necessary for a rigid-endoscope optical system that, because of a small depth of field, when the endoscope is operated to perform a surgical operation, the imaging optical system 6 is moved back and forth along the optical axis so that the focusing operation is frequently carried out. This practice is not favorable. Recently, in order to improve the depth of field, the variable stop 31 is placed adjacent to the position of the pupil transmitted by the relay system of the endoscope so that when a distant object is observed, the stop 31 is opened to make the object bright, while when a nearby object is observed, it is stopped down because brightness is excessive.

In this case, however, the electric drive paths 32 for driving the stop 31 are required, and for the structure shown in FIG. 2, the electric contacts 33 are required to connect the TV adapter 25 with the TV camera head 27. This structure is inconvenient for sterilization. In the case of an endoscope for medicine in particular, a thorough sterilization treatment of the endoscope after use is indispensable for the prevention of an infectious disease.

Although in the past the sterilization treatment has been made using a gas, such as EOG, and wash water as previously described, sterilization gases are virulently poisonous, as is well known, and in order to ensure the safety of sterilization work, the work becomes elaborate. Furthermore, there is the problem that waste treatment of the wash water is expensive.

In recent years, therefore, a heat sterilization (autoclaving) method which does not require such elaborate working methods is chiefly used in the sterilization work of the endoscope apparatus.

However, for example, in the attachment camera which is removably mounted to the eyepiece section of the endoscope to form the endoscope image, its watertight property is sufficient for ordinary use, but it is difficult to completely seal the camera under conditions of high temperature and pressure in autoclaving treatment. Thus, steam is admitted into the camera and tarnish develops in the optical system. Moreover, for electronic parts, degradation and corrosion may be caused.

In the conventional apparatus, on the other hand, when the autoclaving treatment is made, the electric contacts 33 shown in FIG. 2 cannot be provided on the surfaces of the apparatus, and it is also impossible that, as has been done in the past, for a knob to be mounted outside the TV camera head 27 to manually move the imaging optical system 6.

Thus, as a solution of the above description, FIG. 3 shows a typical structure of a conventional imaging apparatus for endoscopes using an attachment TV camera which has heat resistance to the autoclaving treatment. In this figure, reference numeral 34 denotes a TV camera head and 40 and 42 denote transparent glass (for example, sapphire glass) covers having heat resistance. The endoscope image, after passing through the transparent glass cover 42, is formed on the image sensor 16 by the imaging optical system 6. The filter unit 10, including a low-pass filter and an infrared cut filter, is placed in the optical path. An auto-iris device 38 and the imaging optical system 6 are covered with three layers, formed in order from the inside, of a conductive layer (for example, having the film of an metallic sheath on a cylindrical member) 35, an insulating layer 36, and a metallic layer 37. Reference numeral 39 represents an end supporting member, which holds the three layers.

However, this TV camera head, which has a multi-layer structure, has the problem that it cannot be designed so that, as in the prior art, the imaging optical system 6 is moved by a knob from the outside thereof to perform the focusing operation.

FIG. 4A shows another structure of the conventional imaging apparatus for endoscopes. This apparatus, like that shown in FIG. 3, is such that the TV photographic adapter is constructed integral with the TV camera head. Although the frequency of focusing decreases, work for performing the focusing operation is not eliminated. In the imaging apparatus for endoscopes, as shown in FIG. 4A, a stop unit 46 having the auto-iris 38 is usually shaped into a cylindrical form extending along the optical axis in order to intend radial compactness. Further, a lens barrel 47 holding the imaging optical system 6 is incorporated in the stop unit 46 and is provided with a focus adjusting knob 48. By operating the focus adjusting knob 48 from the outside of an outer frame 45a of the TV camera head 45, the imaging optical system 6 can be moved along the optical axis. FIG. 4B depicts the focus adjusting knob 48 viewed from the side of the TV camera head 45.

The endoscope image captured by the endoscope 1 passes through the glass cover 40 having heat resistance provided at the rear of the endoscope 1 and the glass cover 42 likewise having heat resistance provided at the top of the TV camera head 45, and then is formed on the CCD 16 by the imaging optical system 6. The filter unit 10, including a low-pass filter and an infrared cut filter, is placed immediately before the CCD 16 in the optical path. The focusing operation of the imaging optical system 6 in this imaging apparatus for endoscopes is performed by moving the focus adjusting knob 48 attached to the lens barrel 47 in the directions of arrows of the figure to shift the imaging optical system 6 along the optical axis with respect to the CCD 16.

The optical system used in the imaging apparatus for endoscopes is adapted to receive light not coming directly from an object as in a camera, but emerging from the endoscope. There is a pupil in the endoscope and it is required that the position of the pupil is made to practically coincide with that of the stop of the TV camera head. Hence, even where lenses are moved for focusing, the stop cannot be moved very well. In the apparatus shown in FIG. 4A, when the focusing operation is performed, the stop (auto-iris 38) remains fixed and only the imaging optical system 6 is moved. It is thus required that the lenses are provided in a frame separate from the stop unit 46. Hence, the frame member supporting the imaging optical system 6 has the structure with at least three layers, and the imaging optical system 6 becomes shaky, thus causing decentering. Moreover, since such a conventional apparatus requires the lens barrel 47 and the focus adjusting knob 48, the number of parts is increased.

In the imaging apparatus for endoscopes, the stop has the function of determining the place where the chief ray of the imaging optical system passes. If the relative positions of the stop and the imaging optical system are changed, the ray will traverse a place different from a predetermined place and aberration will be varied or aggravated. It is therefore favorable that the positional relation between the stop and the imaging optical system remains unchanged as far as possible. However, since the conventional apparatus shown in FIG. 4A is designed so that the imaging optical system 6 is moved along the optical axis while fixing the auto-iris 38, the height of the ray passing through the imaging optical system 6 is largely changed by the focusing operation, and aberration of the periphery of the image plane is liable to deteriorate.

In view of the compactness of the TV camera head 45 attached to the endoscope 1, it is necessary to reduce the outer diameter of the imaging optical system 6, corresponding to the thickness of the lens barrel 47 in the stop unit 46. Consequently, an effective marginal beam of the imaging optical system 6 comes to exhibit a tendency to vignetting, and a reduction in the amount of marginal light and ghost and flare caused by the ray striking upon the lens barrel 47 are liable to occur. Conversely, in view of the vignetting of the light beam, if the outer diameter of the stop unit 46 is increased, the compactness of the apparatus cannot be achieved. This is contradictory to the property of the imaging apparatus for endoscopes that its radial dimension must be reduced to a minimum.

SUMMARY OF THE INVENTION

It is, therefore, an object of the present invention to provide an imaging apparatus for endoscopes which has autoclaving resistance, is capable of making a focus adjustment, and facilitates a change in magnification for observation of an endoscope image.

Another object of the present invention is to provide an imaging apparatus for endoscopes in which a variable stop (auto-iris) is placed, an optimum focusing operation is performed, and sterilization treatment is possible.

Still another object of the present invention is to provide an imaging apparatus for endoscopes in which when a focus is approximately taken in an endoscope, an optimum focusing operation is performed only by actuating an auto-iris device and a good image can be obtained.

According to one aspect of the present invention, the imaging apparatus for endoscopes includes an endoscope, a TV camera head incorporating a solid-state image sensor, and a TV photographic adapter incorporating an optical system for forming an endoscope image on the solid-state image sensor. At least one of the TV camera head and the TV photographic adapter is sealed with dampproof members. The apparatus may be designed to use a throwaway (or disposable) TV camera head and to seal the TV photographic adapter with dampproof members so that optical filters are arranged therein.

Further, it is desirable that the apparatus of the present invention is constructed so that a coupling device having a sterilized sheath for covering the TV camera head or the TV photographic adapter can be connected. The apparatus is equipped with a mechanism for changing the distance between the optical system and the solid-state image sensor along the optical axis.

According to another aspect of the present invention, the imaging apparatus for endoscopes includes an adapter which is removably mounted to an eyepiece section of an endoscope and which has a lens member for changing the degree of convergence or divergence of a light beam emerging from the eyepiece section, and a watertight camera which is removably mounted to the adapter and has an imaging optical system and an image sensor therein. When the camera is mounted through the adapter to the eyepiece section of the endoscope, the distance between the adapter and the camera is changed and thereby a focusing operation is performed.

Further, the apparatus of the present invention, instead of using the adapter, is capable of using inter-changeably a plurality of adapters, each having lens members of a different focal length. The lens members can be replaced by a single lens. Furthermore, the camera is provided with a stop whose aperture size is variable.

According to still another aspect of the present invention, the imaging apparatus for endoscopes includes an endoscope for relaying an object image through an observation optical system and a TV camera removably mounted to the endoscope. The TV camera is equipped with an imaging optical system for re-forming the final image relayed by the endoscope, a stop unit having a stop whose aperture size is variable, and an image sensor. At least one of lenses constituting the imaging optical system is attached to the stop unit so that the focusing operation is performed by changing a distance from the stop and the lens to the image sensor.

Further, the apparatus of the present invention is designed so that the image sensor is moves along the optical axis and thereby the distance between the lens and the image sensor can be changed. Still further, by moving the stop and the lens along the optical axis, the distance between the lens and the image sensor can be changed.

These and other objects as well as the features and advantages of the present invention will become apparent from the following detailed description of the preferred embodiments when taken in conjunction with the accompanying drawings.

Figure 16:
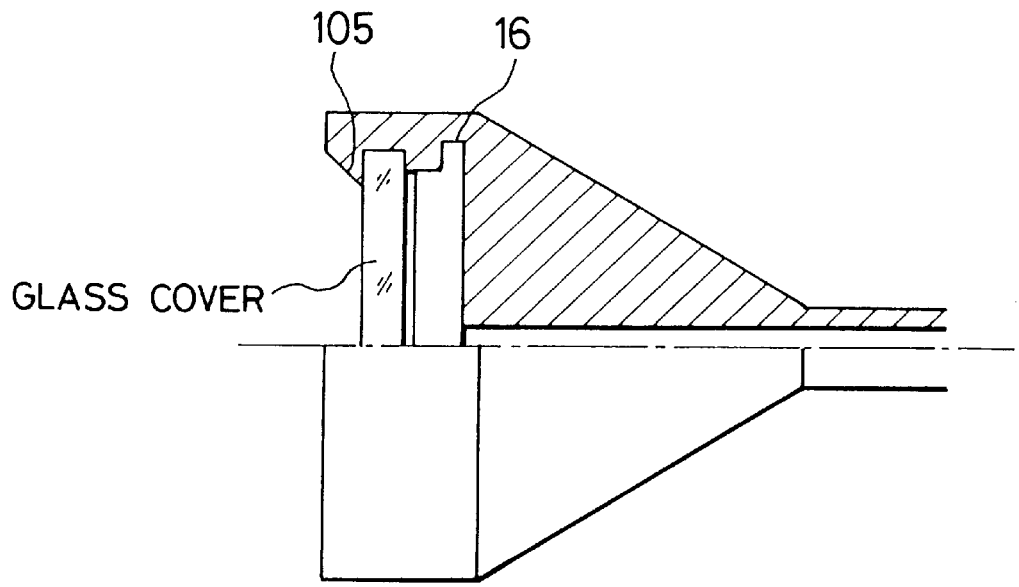
Figure 17:
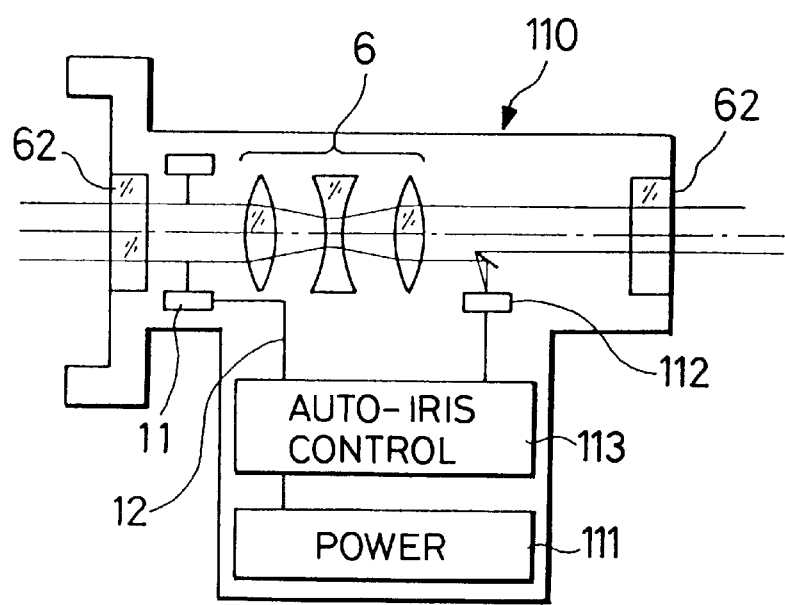
Figure 18:
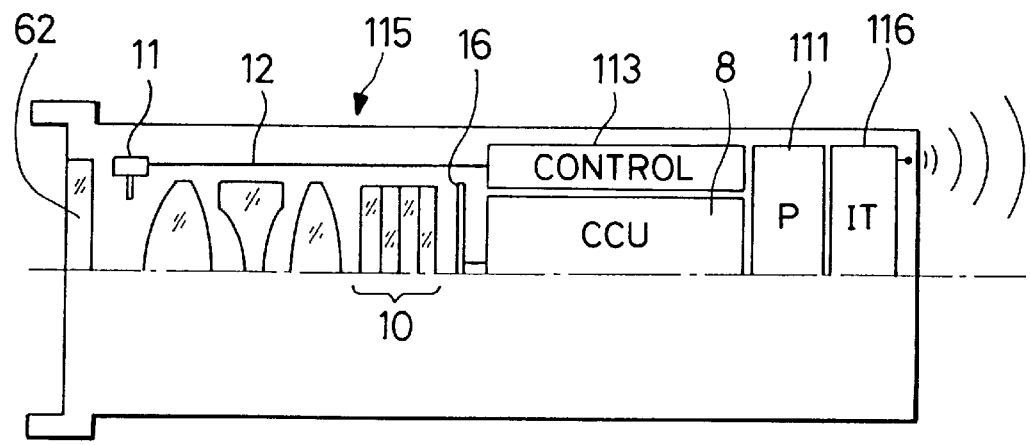
Figure 19:
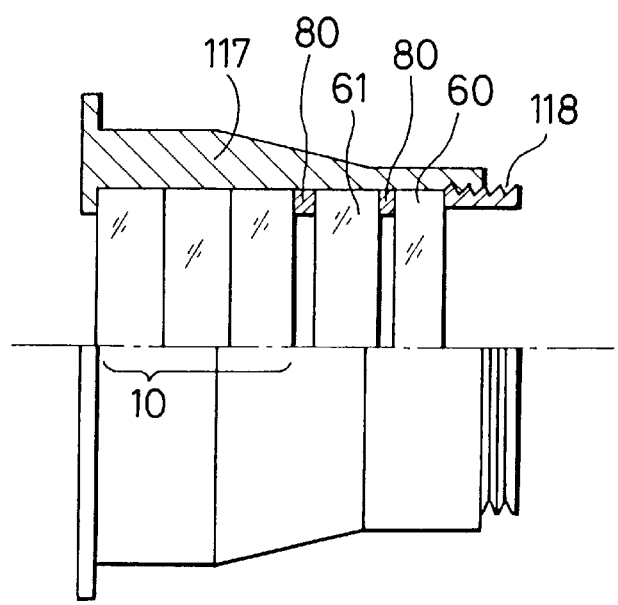
Figure 20A:
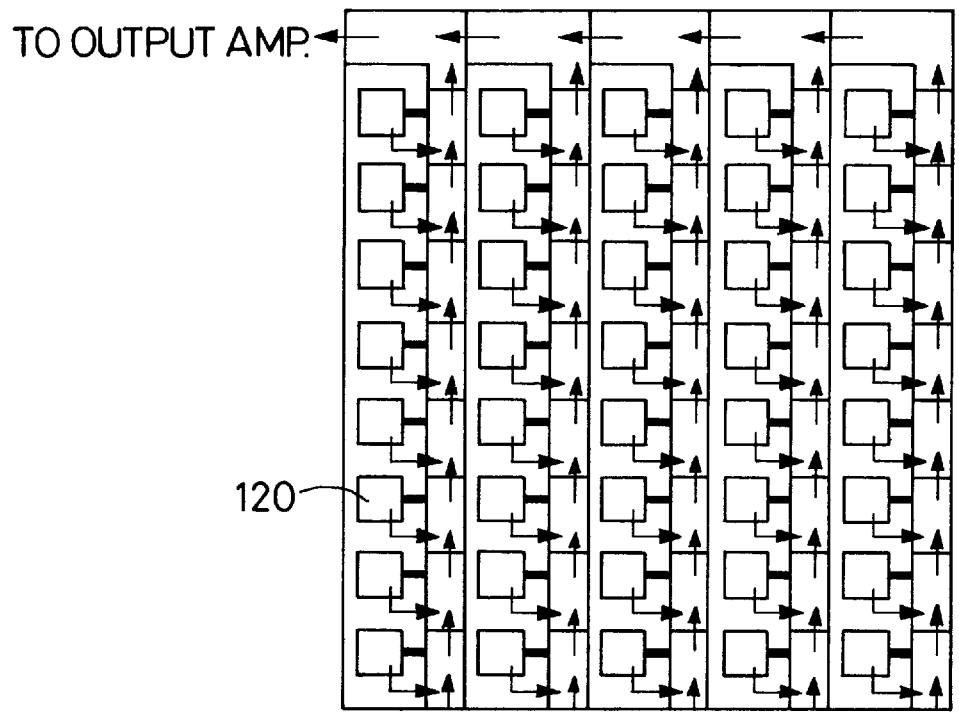
Figure 20B:
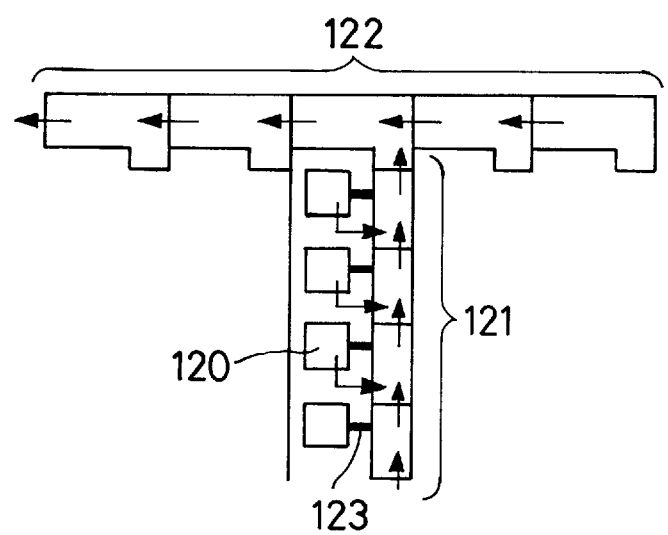
Figure 23:
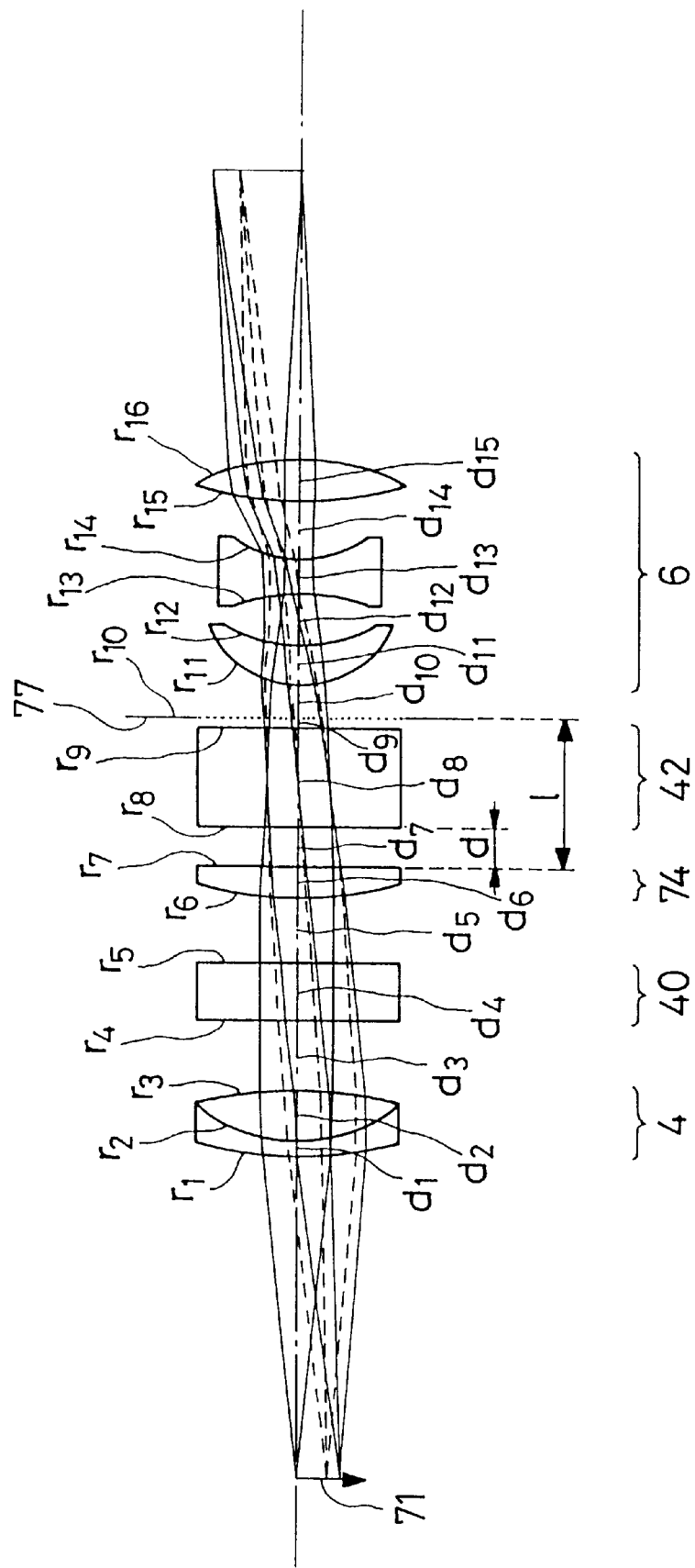
Figure 24:
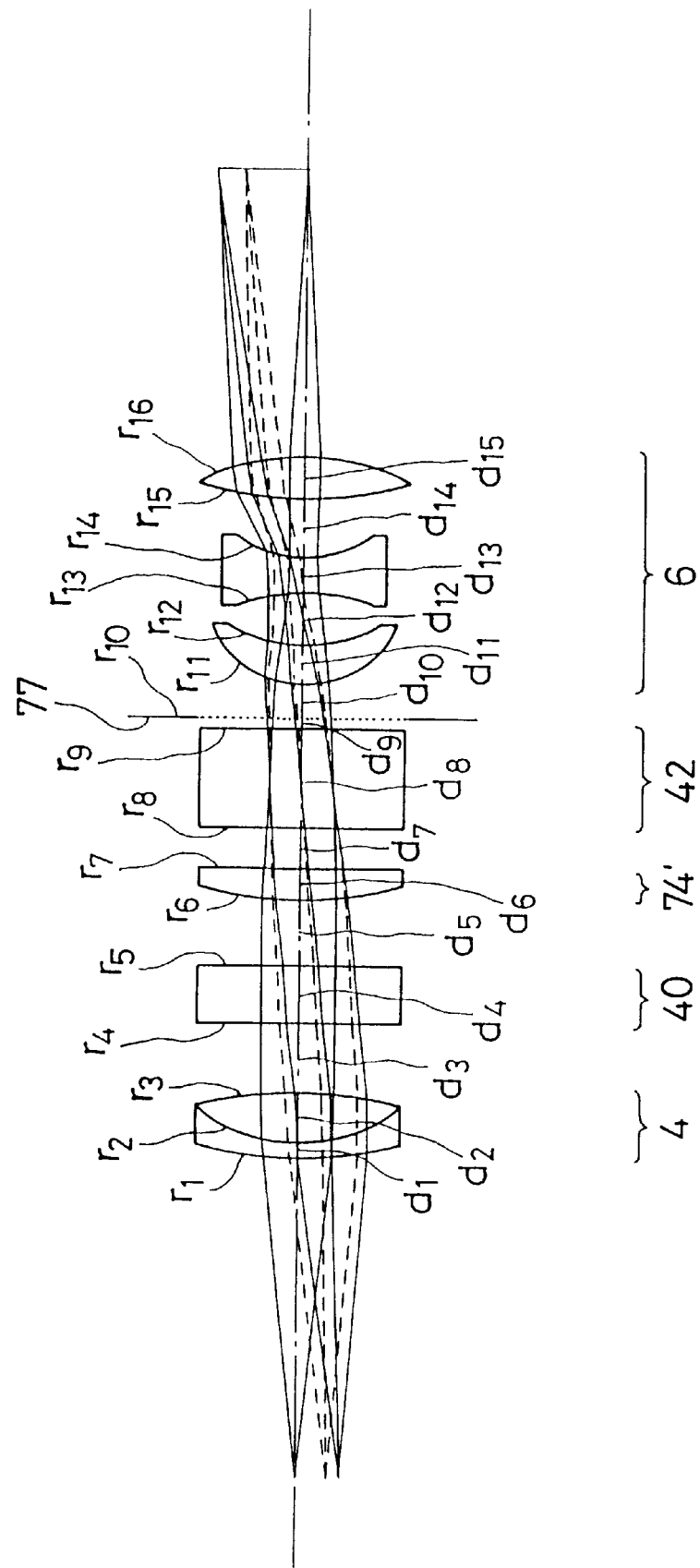
Figure 25:
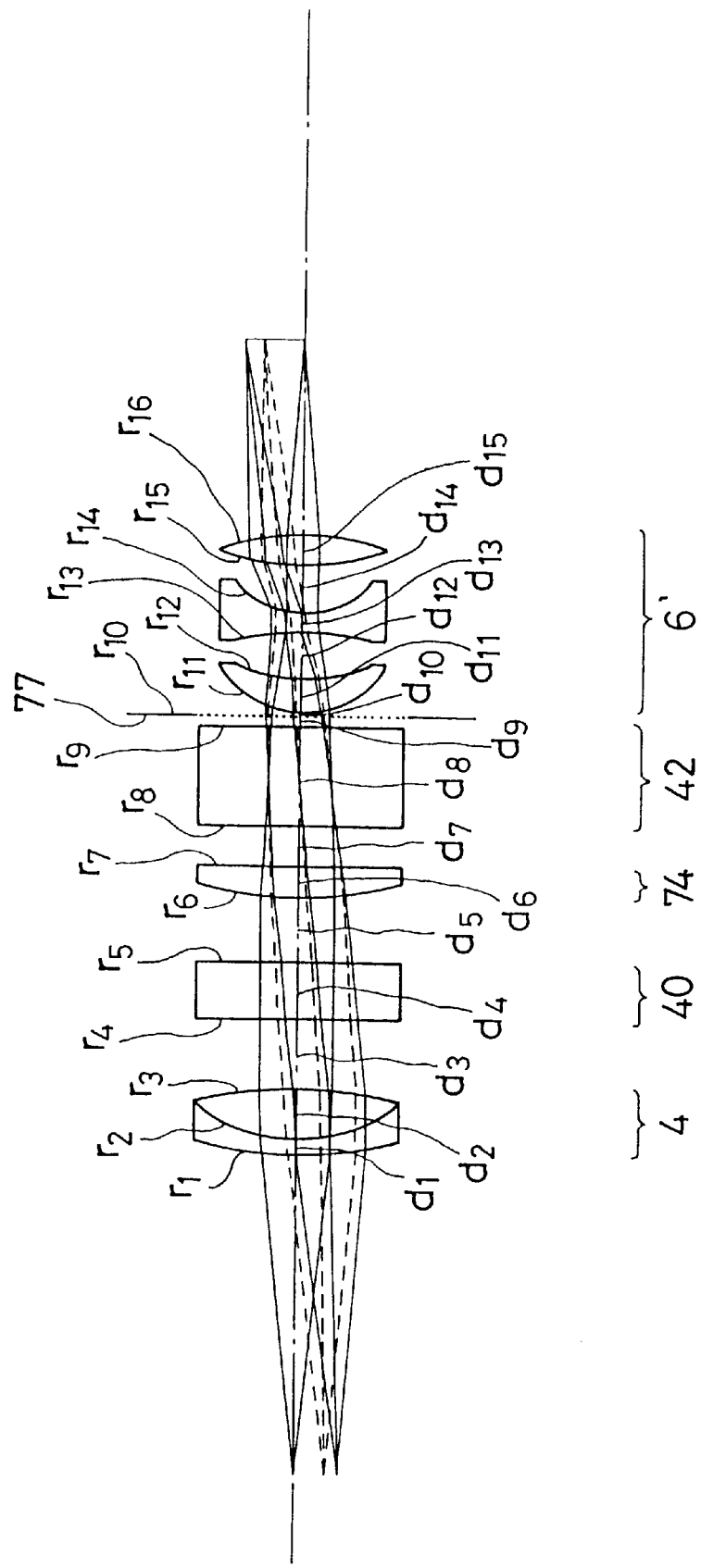
Figure 26:
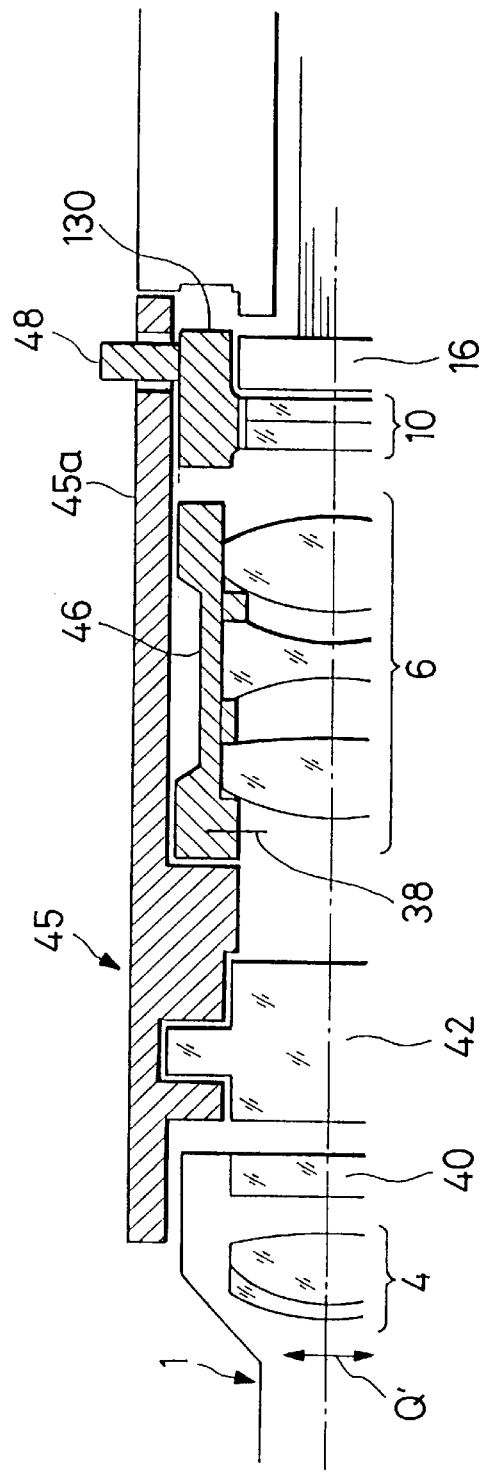
Figure 27:
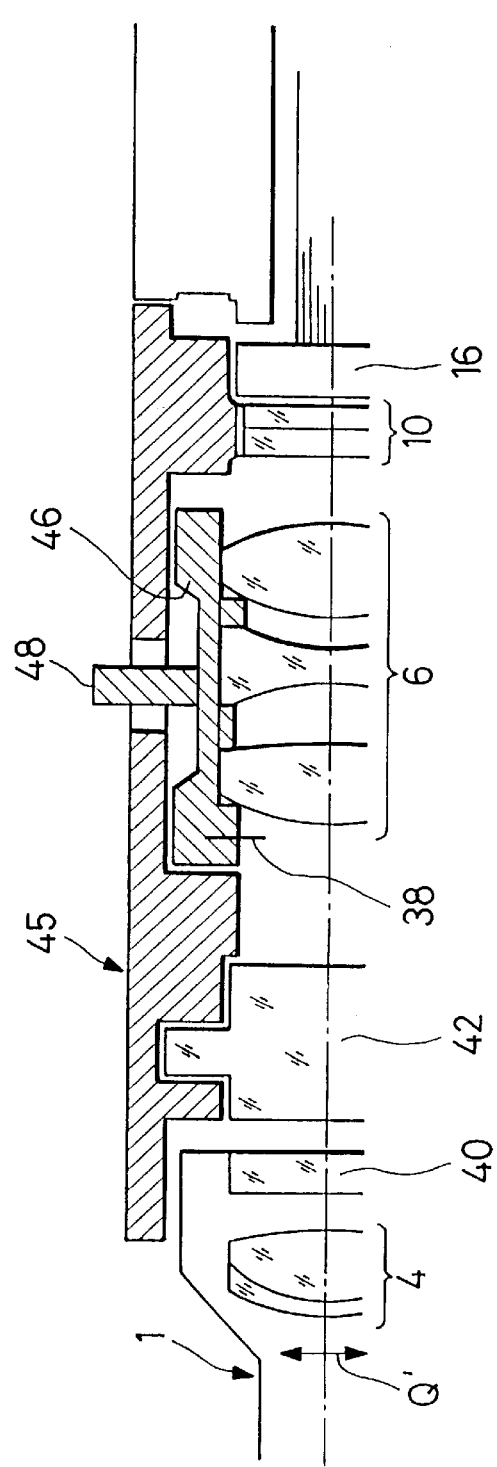
Figure 28A:
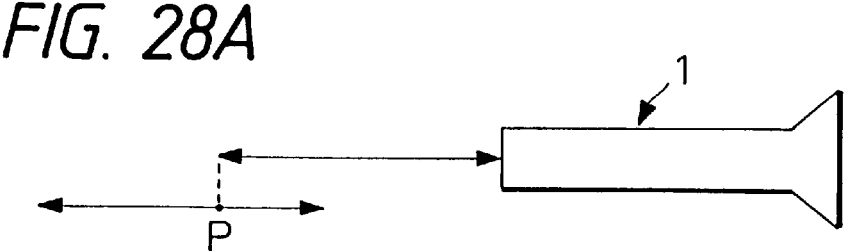
Figure 28B:
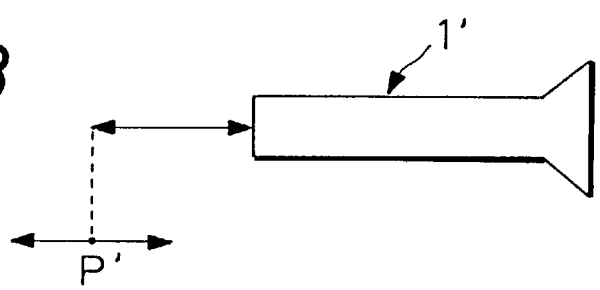
Figure 29A:
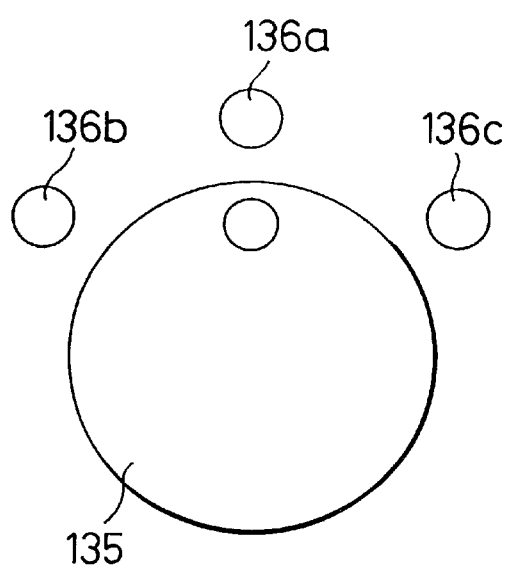
Figure 29B:
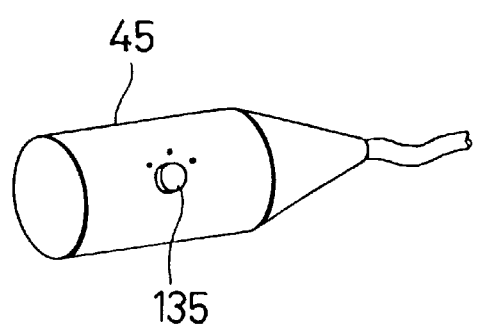
Figure 30:
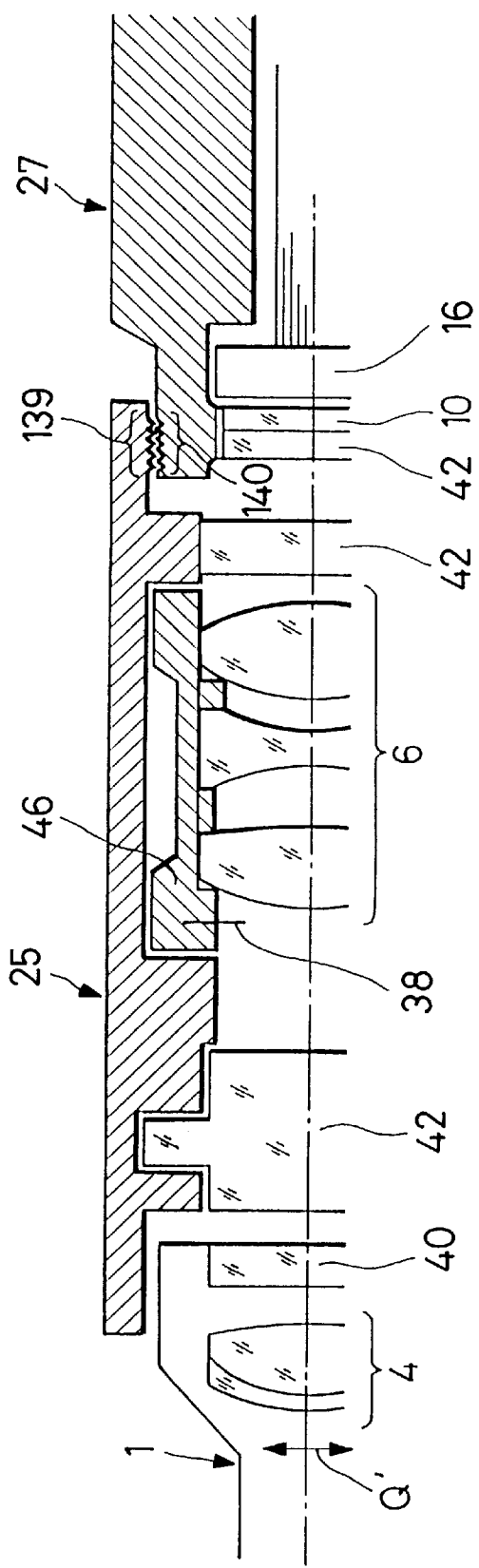
Figure 31:
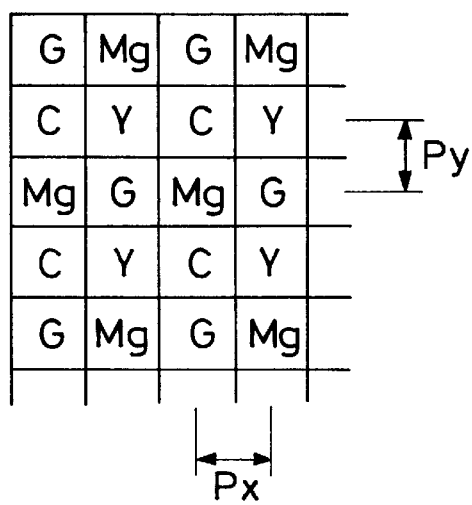
Figure 33:
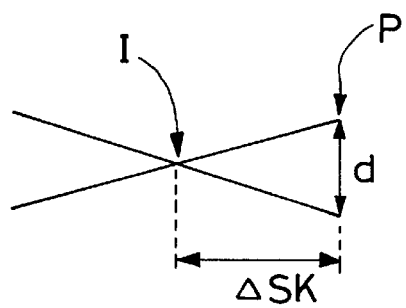
Figure 32:
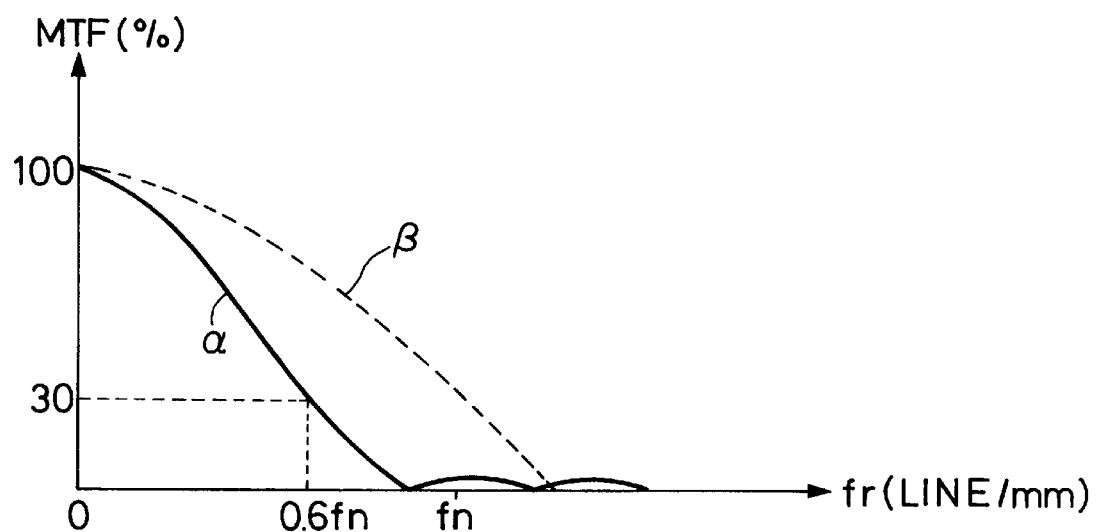
Figure 34:
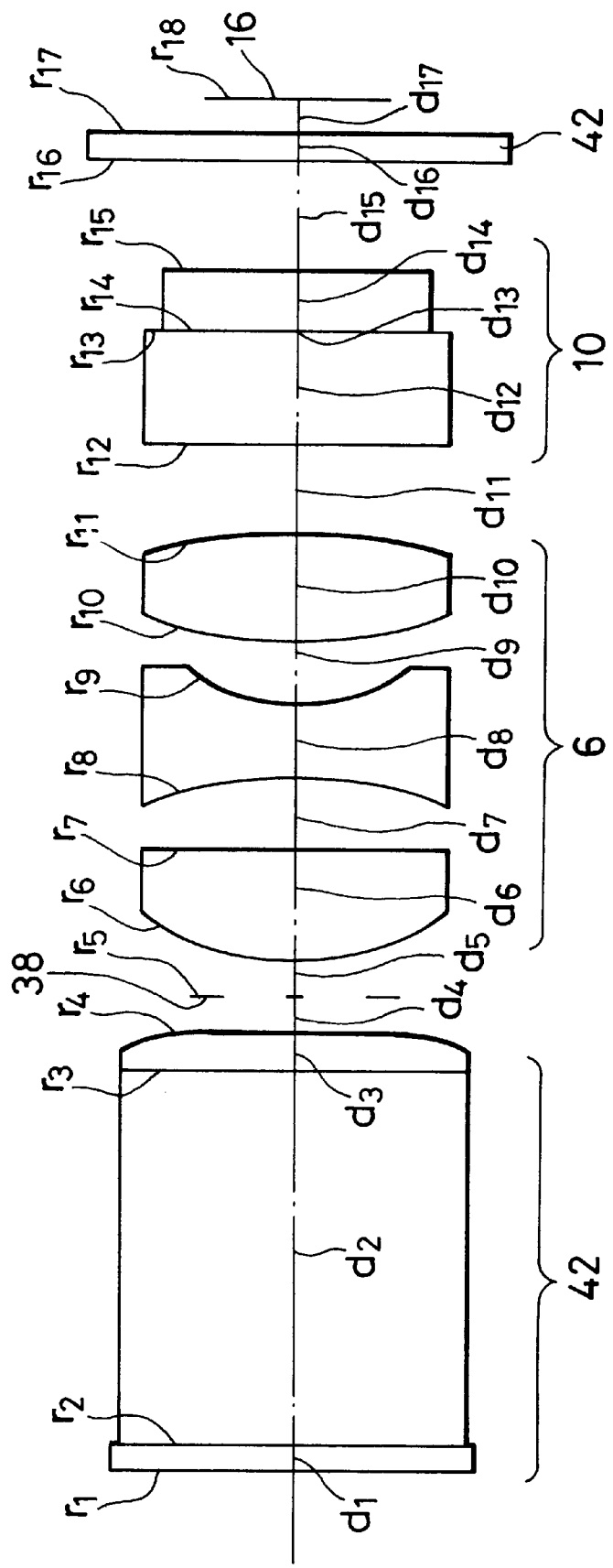

FIG, 15 is a chart for explaining another systematic construction;

FIG. 16 is a partially sectional view showing a TV camera head having a mask for eliminating ghost and flare;

FIG. 17 is a sectional view showing the construction of a TV photographic adapter having an auto-iris device used in the apparatus of the present invention;

FIG. 18 is a sectional view showing the construction of a TV camera head having an auto-iris device used in the apparatus of the present invention;

FIG. 19 is a sectional view showing the arrangement of a filter unit used in the apparatus of the present invention;

FIGS. 20A and 20B are a schematic view showing the photoelectric converting surface of a CCD image sensor of an interline system;

FIGS. 21A, 21B, and 21C are cross-sectional schematic views showing the imaging surface of the CCD with filters capable of favorably correcting chromatic aberration;

FIG. 22 is a view for explaining the array of the filters shown in FIGS. 21A–21C;

FIG. 23 is a view showing the lens arrangement of an optical system of a third embodiment in the present invention;

FIG. 24 is a view showing the lens arrangement of an optical system of a fourth embodiment in the present invention;

FIG. 25 is a view showing the lens arrangement of an optical system of a fifth embodiment in the present invention;

FIG. 26 is a view showing the structure of a TV camera head in a sixth embodiment of the apparatus of the present invention;

FIG. 27 is a view showing a modification of the sixth embodiment;

FIGS. 28A and 28B are views for explaining the shifts of focusing positions varying according to endoscopes;

FIGS. 29A and 29B are views for explaining a dial type focus adjusting mechanism provided in the apparatus of the sixth embodiment;

FIG. 30 is a view showing the structure of a TV camera head in a seventh embodiment;

FIG. 31 is a view for explaining a pixel pitch in a horizontal scanning direction used in the apparatus of the present invention;

FIG. 32 is a diagram showing frequency characteristics relative to an optical low-pass filter;

FIG. 33 is a view showing the positional relation between an imaging position of an endoscope image and an imaging surface;

FIG. 34 is a view showing an optical arrangement in an eighth embodiment;

FIGS. 35A, 35B, 35C, and 35D are views for explaining the change of the aperture size of an auto-iris device shown in FIG. 34; and FIG. 36 is a view for explaining the technique of converting the aperture size of the auto-iris device into a circle to find its minimum limit value.

DETAILED DESCRIPTION OF THE PREFERRED EMBODIMENTS

Before undertaking the description of the embodiments, it will be expedient to explain the function of the imaging apparatus for endoscopes of the present invention in comparison with conventional apparatus.

Figure 5:
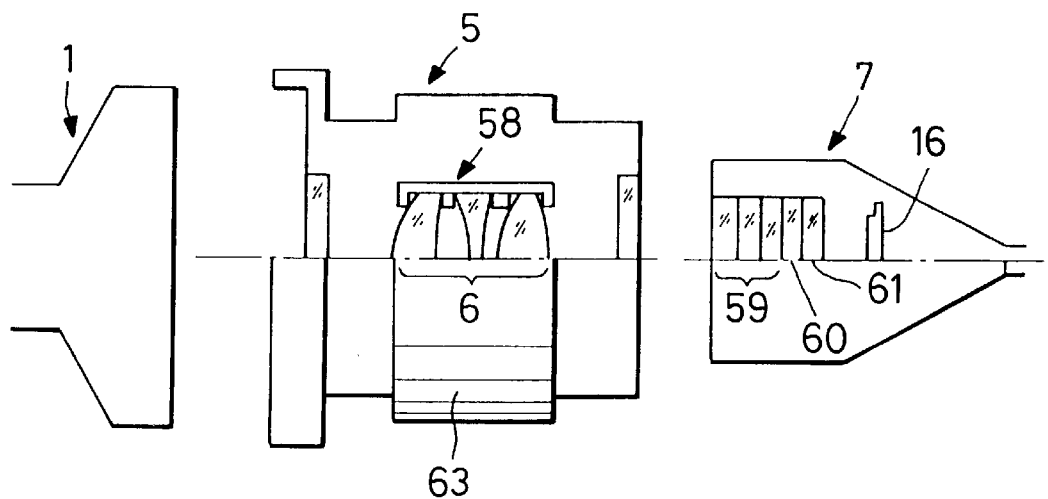
FIG. 5 is a partially sectional view, along the optical axis, showing a conceptual construction of the conventional imaging apparatus for endoscopes.
Figure 3:
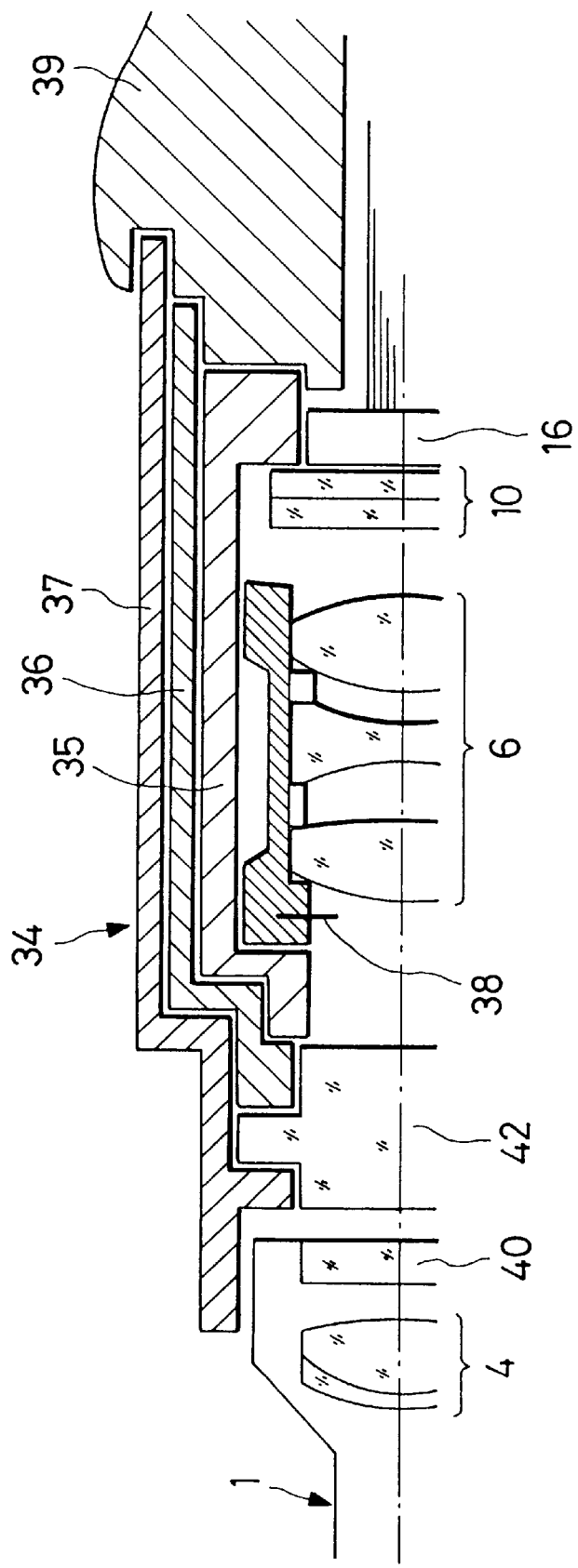
FIG. 3 is a sectional view showing the structure of a TV camera head in the conventional imaging apparatus.
Figure 4A:
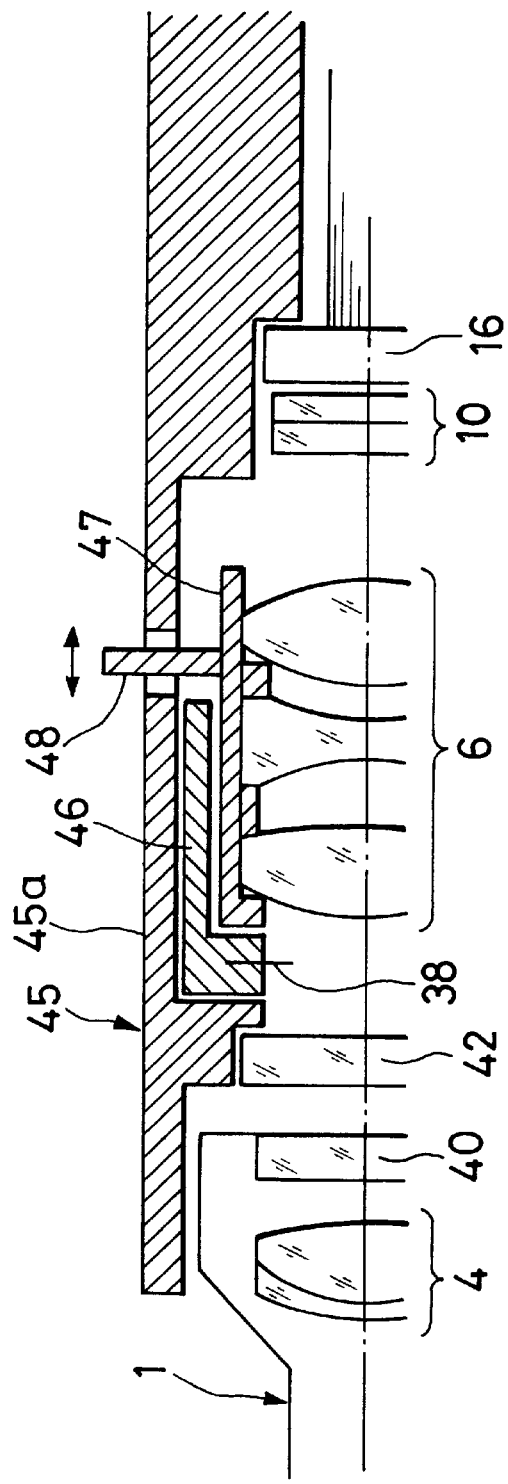
FIGS. 4A and 4B are views showing the structure of another TV camera head.
Figure 4B:
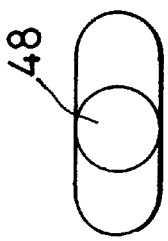

In FIG. 5, the conventional imaging apparatus for endoscopes includes the endoscope 1, the TV photographic adapter 5, and the TV camera head 7. The TV photographic adapter 5 has a lens barrel 58 in which the imaging optical system 6 is encased to form the image obtained by the endoscope 1 on the CCD 16 housed in the TV camera head 7. The TV camera head 7 includes a quartz filter unit 59, a YAG (yttrium aluminum garnet) laser-beam cut filter 60, an infrared cut filter 61, and the CCD 16 which are arranged on the optical axis. This conventional imaging apparatus for endoscopes is designed so that when a focusing ring 63 is rotated concentrically with the optical axis, the lens barrel 58 can be moved along the optical axis by the action of a known cam, not shown, to make the focus adjustment of the endoscope image.

Figure 6:
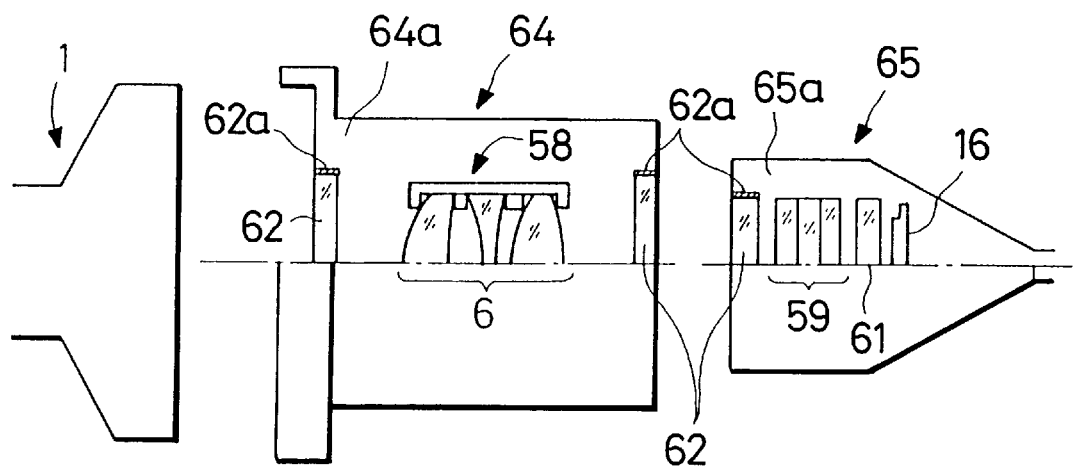
FIG. 6 is a partially sectional view, along the optical axis, showing a conceptual construction of the imaging apparatus for endoscopes of the present invention.

In FIG. 6, on the other hand, the imaging apparatus for endoscopes of the present invention comprises the endoscope 1, a TV photographic adapter 64, and a TV camera head 65. The TV photographic adapter 64 is constructed so that glass covers 62 made of sapphire glass which is excellent in dampproof and weatherproof properties, are arranged on the sides facing the endoscope 1 and the TV camera head 65, and cover frames 62a surrounding the glass covers 62 are soldered to an outer frame 64a of the TV photographic adapter 64 to thereby attain a hermetically sealed structure, with the result that the TV photographic adapter can be treated by autoclaving. Similarly, the TV camera head 65 is such that the sapphire glass cover 62 is placed on the side facing the TV photographic adapter 64, and the cover frame 62a is soldered to a outer frame 65a of the TV camera head 65 to thereby attain a hermetically sealed structure, with the result that the autoclaving treatment can be received by the TV camera head per se.

Thus, in order to obtain autoclaving resistance, the TV photographic adapter 64 used in the apparatus of the present invention is designed so that the imaging optical system 6 is sandwiched between the sapphire glass covers 62, and by changing the distance from the last lens surface of the imaging optical system 6 to the TV camera head 65, the focus adjustment where the endoscope 1 is combined is performed. Furthermore, the TV photographic adapter 64 has a structure suitable for the autoclaving treatment, and thus when magnifications for observation of images are chosen, it is only necessary to replace the TV photographic adapter 64 with another. In this way, the imaging apparatus for endoscopes taking into account the system extension can be realized.

Figure 7:
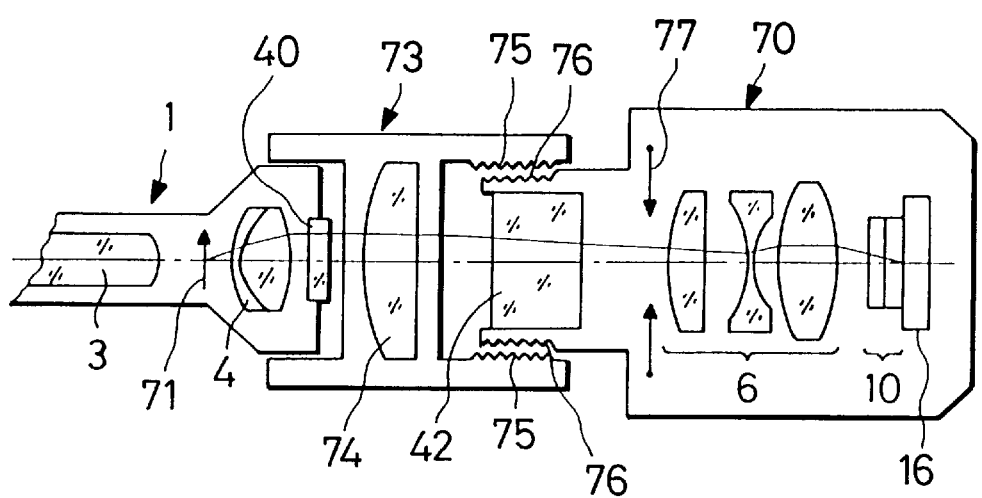
FIG. 7 is a view showing the structure of the imaging apparatus for endoscopes of the present invention.

FIG. 7 depicts the construction of the apparatus according to the present invention, in which the endoscope (rigid endoscope) 1 is mounted to a TV camera head 70 having autoclaving resistance. This endoscope is the same as the conventional one. The apparatus of the present invention is such that a final relay image 71 transmitted by the image transmission system (relay system) 3 of the endoscope 1, after passing through the eyepiece 4 and the glass cover 40, is incident on a front lens unit (focusing lens) 74 and then on a rear imaging lens unit (the imaging optical system 6) of the TV camera head 70 and is formed on the CCD 16. A portion where a focusing adapter 73 is coupled with the eyepiece section of the endoscope 1 is designed so that both are relatively rotatable about the optical axis. Additionally, the connection of the focusing adapter 73 with the TV camera head 70 is provided with screws 75 and 76. Hence, when the focusing adapter 73 is rotated about the optical axis, the TV camera head 70 is moved back and forth along the optical axis. Whereby, the distance between the focusing adapter 73 and the TV camera head 70 is changed and the focusing operation can be performed. Reference numeral 77 designates an auto-iris device, which is provided in the TV camera head 70 having a watertight structure.

Figure 2:
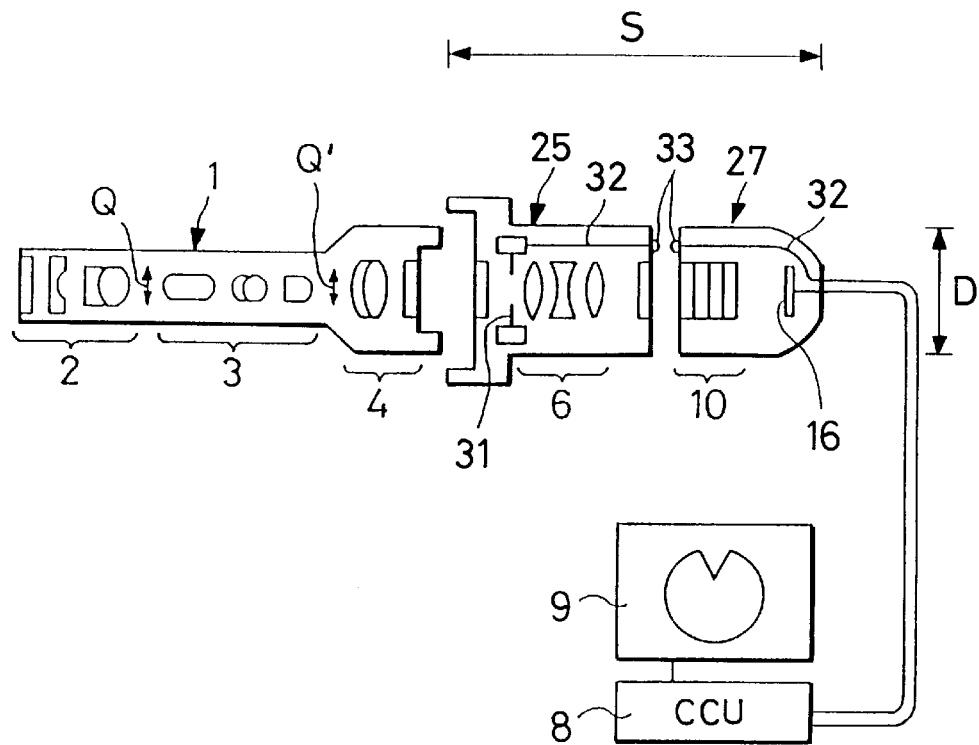
FIG. 2 is a view showing the construction of the conventional imaging apparatus using an attachment TV camera.

The conventional TV camera head 27, as shown in FIG. 2, has autoclaving resistance, but is not designed to shift the position of the imaging optical system 6 with respect to the CCD 16. Moreover, an imaging point formed by the eyepiece 4 is close to infinity and thus, even though the distance between the eyepiece 4 and the imaging optical system 6 is varied, the focusing operation cannot be performed.

In the apparatus of the present invention, however, the construction shown in FIG. 7, makes focusing possible and allows the observing distance of the endoscope 1 to be changed. In addition, the TV camera head 70, as mentioned above, has a fully watertight structure. Thus, the front lens unit 74 is completely divided from the imaging optical system 6 by the glass cover 42 having resistance. In order to acquire heat resistance to autoclaving, it is desirable that the glass cover is constructed not with a common optical member, but of crystal glass like sapphire, quartz, or rock crystal. In this way, the attachment TV camera mounted to the endoscope 1 can be provided with the auto-iris device and autoclaving resistance.

Figure 8:
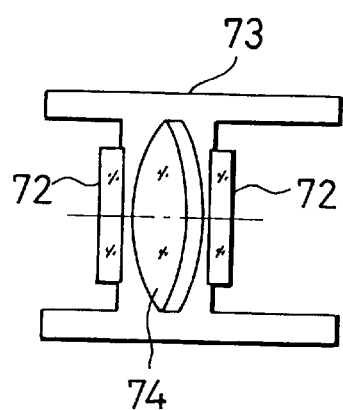
FIG. 8 is a view showing a focusing adapter having autoclaving resistance.

The focusing adapter 73 also needs autoclaving resistance. For this, it is required that the front lens unit 74 is made of crystal glass having autoclaving resistance. However, where a common optical glass is used with the intention of suppressing chromatic aberration to some extent, as shown in FIG. 8, both ends of the front lens unit 74 may be hermetically constructed with crystal glass members 72. By this structure, the focusing adapter 73 can be provided with autoclaving resistance. The focusing adapter 73 is typically discarded after use as a matter of course. In this case, it is desirable that the front lens unit 74 be plastic or the like.

Figure 9:
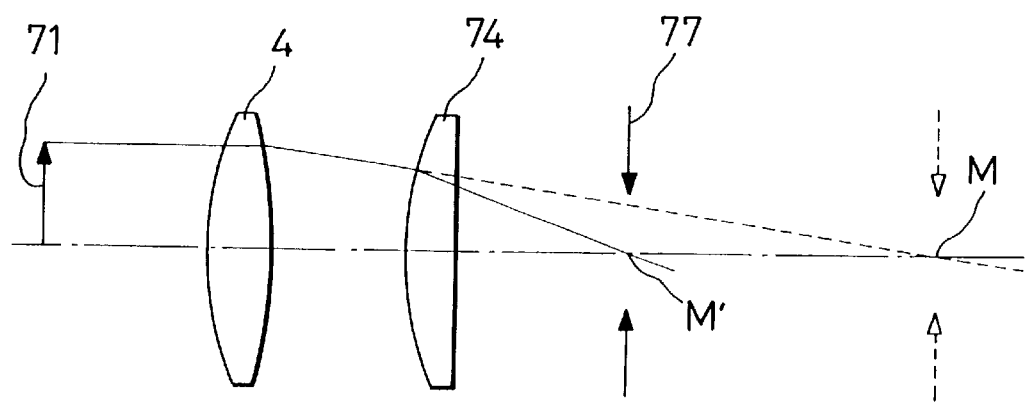
FIG. 9 is a view showing a paraxial arrangement of an optical system In FIG. 7.

In FIG. 9, the exit pupil of the final relay image 71 is close to infinity in the case of the rigid endoscope, and the so-called eyepoint lying behind the eyepiece 4 is located adjacent to a focal point M of the eyepiece 4. The conventional apparatus shown in FIG. 2 is such that the auto-iris device can be located at the position of the focal point M. In the apparatus of the present invention, however, the front lens unit 74 for focusing is provided, so that the eyepoint is situated closer to the eyepiece 4. In this case, although focusing becomes possible, the auto-iris device 77 must be located at a position M' because the eyepoint is closer to the eyepiece 4, and the distance between the eyepiece 4 and the auto-iris device 77 will be diminished. Consequently, where the front lens unit 74 is moved for focusing, its focusing range is limited. Hence, it is desirable that the front lens unit 74 is of the smallest possible thickness, preferably a single lens.

Figure 10:
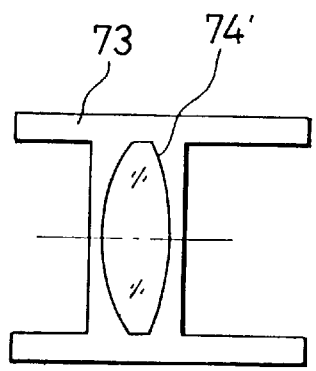
FIG. 10 is a view showing an exchangeable focusing adapter using a single lens.

Thus, it is favorable that several kinds of focusing adapters are previously provided and are used interchangeably with one another. Using FIG. 10, reference is made to each focusing adapter in this case. This focusing adapter, instead of the front lens unit 74 shown in FIG. 7, uses a front lens unit 74'. The front lens unit 74' is desirable to be a single lens, and may be designed so that the focal length of the single lens is changed with respect to the front lens unit 74 or the single lens is configured as a plano-convex, biconvex, or meniscus lens to shift its principal point. Where it is required that aberration which cannot be completely corrected by the image transmission optical system of the endoscope be corrected by the focusing adapter 73, a cemented lens, such as that shown in FIG. 8, may be used.

Figure 11:
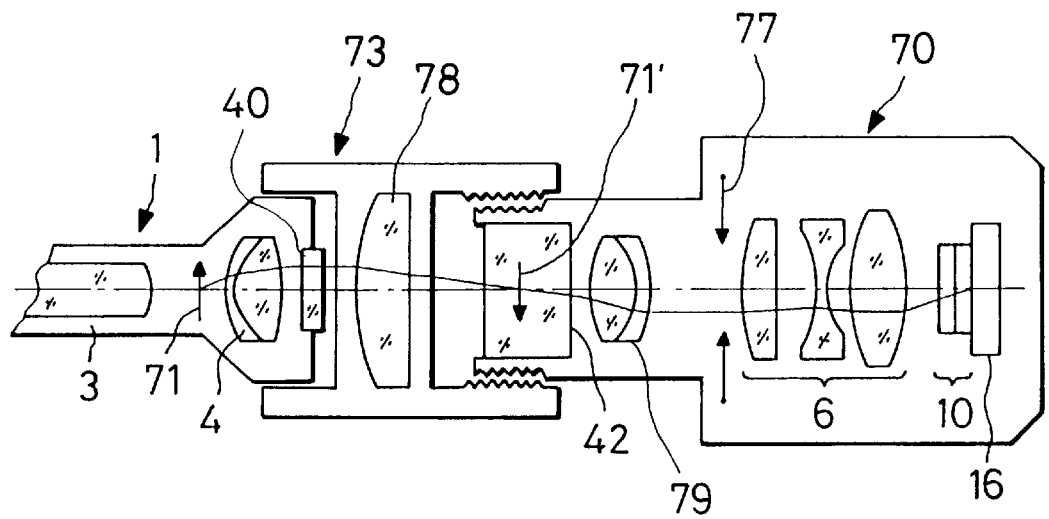
FIG. 11 is a view showing a modification of the apparatus showing in FIG. 7

As a modification of the apparatus shown in FIG. 7, an apparatus depicted in FIG. 11 is considered. The apparatus of FIG. 7 (hereinafter referred to as an apparatus A) is such that an object point close to infinity is made finite by the front lens unit 74 in the focusing adapter 73, while the apparatus of FIG. 11 (hereinafter referred as to an apparatus B) is such that the final relay image 71 transmitted by the image transmission system 3 of the endoscope 1 is further relayed by the eyepiece 4 and a focusing lens 78. Specifically, the apparatus B is designed so that the object image is formed ahead of the auto-iris device 77 placed in the TV camera head 70 by the optical system of the front lens unit. In FIG. 11, reference numeral 71' represents a further once-relayed image of the final image 71 relayed by the relay system. It is desirable that the relayed image 71' is formed at a place where the images of dust particles are hard to fall on the surface of a prism or lens, for example, inside the glass cover 42 or the lens. Although the relative positions of the image 71' and the glass cover 42 vary with focusing, it is favorable that the relative positions differ as to the entire focusing range. In this case, it is needless to say that the focusing adapter 73 can be replaced with another as in the apparatus A. Also, reference numeral 79 denotes a front lens unit for making light nearly parallel to the optical axis.

If the focusing adapter 73 of the apparatus A and B is merely used as an exchangeable lens for diopter to digitally change the observation distance even though the focusing operation is not required, it will not cause inconvenience. Moreover, because the auto-iris device 77 is mounted, the depth of field is completely obtained with respect to the object to be observed even in a pan-focus state.

For the merits and demerits of the apparatus A and B, the apparatus A, over the apparatus B, can be very compact and have a small number of lenses. The apparatus B, on the other hand, requires a further relay of the image and thus must be made larger accordingly. However, for the number of degrees of positional freedom of the auto-iris device, the apparatus B is larger. The eyepoint of the endoscope In the apparatus A, as already explained with reference to FIG. 9, is situated outside the TV camera head, and therefore it is difficult that the position of the auto-iris device is made to completely coincide with that of the eyepoint. In the apparatus B, by contrast, although the image is once-relayed, the pupil of the endoscope is also once-relayed, and the auto-iris device can be placed at the position of the relayed pupil.

In the imaging apparatus for endoscopes of the present invention, the imaging optical system is attached to a stop unit in order to maintain a constant positional relationship between (part of) the imaging optical system incorporated in the TV camera head and the stop. This arrangement does away with the need for the lens frame lying inside the stop unit, thus doubling the role of the frame structure for supporting the imaging optical system. Hence, the outside diameter of the TV camera head can be reduced by the thickness corresponding to this unnecessary lens frame, and the compactness of the apparatus can be achieved. Alternatively, if the outside diameter of the TV camera head is made identical with that of the conventional apparatus, the outside diameter of the imaging optical system can be made larger, and the vignetting of light and the production of ghost and flare light will be prevented, with a resulting good image for observation.

Further, in the imaging apparatus for endoscopes of the present invention, the stop and at least one the lenses constituting the imaging optical system are fixed to the same frame (stop unit). This is because, in the TV camera head for endoscopes, all of the lenses constituting the imaging optical system are not necessarily incorporated in the stop unit. Also, if an attempt is made to incorporate other lenses overflowing the stop unit in a lens frame similar to the stop unit, a new lens frame will be required. This is unfavorable because the number of parts is increased and the imaging optical system becomes liable to produce shaking.

In addition, the apparatus of the present invention, as mentioned above, is such that since at least one of the lenses constituting the imaging optical system is fixed to the same frame as the frame provided with the stop, the number of lenses moving with the stop is very small compared with the conventional apparatus and aberration is hard to vary. If the stop and all of lenses constituting the imaging optical system can be housed in the same frame, this is more favorable.

Still further, in the apparatus of the present invention, the stop is constructed as the auto-iris (variable stop) device, and thus if a focus is roughly taken once in the endoscope, an optimum focusing operation can be performed only by actuating the auto-iris device. Also, if the apparatus is provided with autoclaving resistance, it can be used for medicine.

In accordance with the embodiments shown in the drawings, the present invention will be explained in detail below. Also, like reference numerals are used for members having like functions with the conventional apparatus.

First Embodiment

Figure 12:
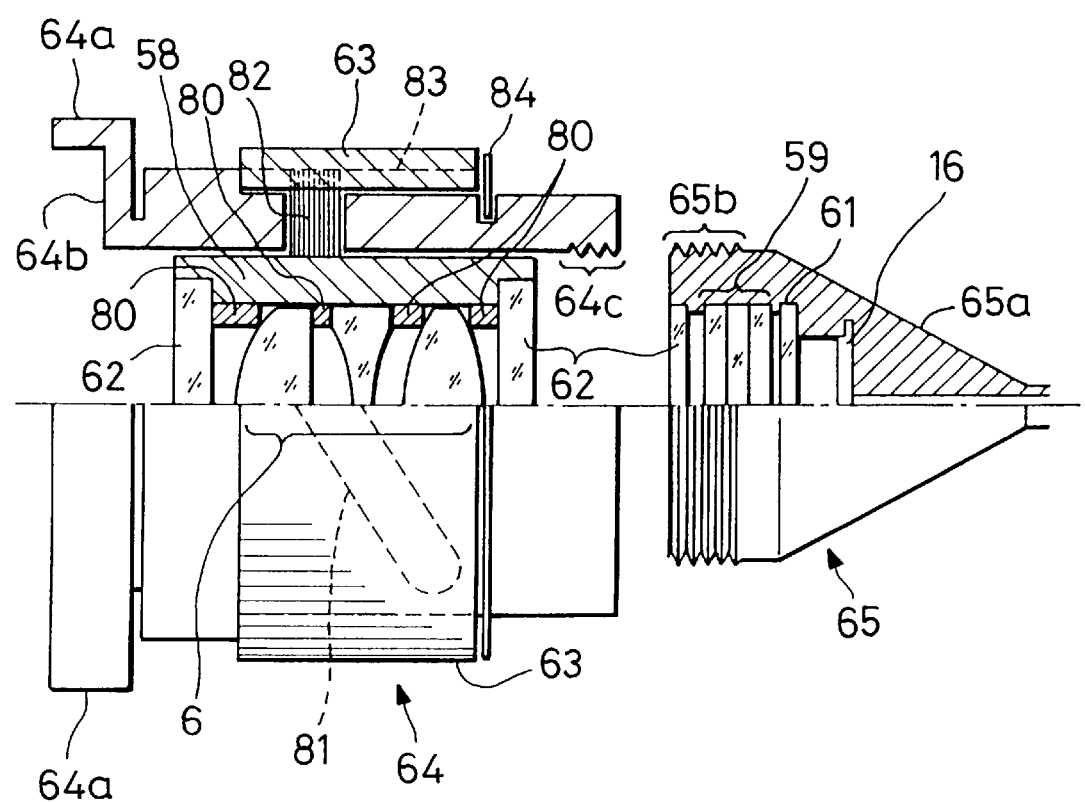
FIG. 12 is a view showing the structure of a first embodiment of the imaging apparatus for endoscopes according to the present invention.

FIG. 12 shows the structure of the first embodiment of the imaging apparatus for endoscopes according to the present invention. In this embodiment, the imaging apparatus for endoscopes includes an endoscope, not shown; the TV adapter 64; and the TV camera head 65. In this case, the endoscope is set up in an endoscope mounting portion 64b of the outer frame 64a of the TV photographic adapter 64. The TV camera head 65 is mounted in the TV photographic adapter 64 by engaging a screw 65b provided on the outer frame 65a with a screw 64c provided inside the outer frame 64a of the TV photographic adapter 64.

In FIG. 12, the object image transmitted from the endoscope not shown (the left of the figure) passes through the imaging optical system 6 disposed in the TV photographic adapter 64 and, after traversing the quartz filter 59 and the infrared filter 61 housed in the TV camera head 65, is formed on the CCD 16 housed in the TV camera head 65. The imaging optical system 6 is encased in the lens barrel 58, and individual lenses constituting the imaging optical system 6 are fixed by spacers 80. Moreover, the lens barrel 58 is hermetically sealed through both sides facing the endoscope and the TV camera head 65 by the sapphire glass covers 62, so that water vapor can be prevented from entering the TV photographic adapter 64 during the autoclaving treatment. The outer frame 64a of the TV photographic adapter 64 is provided with a cam groove 81, which is slidably engaged with a cam pin 82 attached to the lens barrel 58. The cam pin 82 can be slid, in the direction of the optical axis, along a keyway 83 slotted inside the focusing ring 63. A rotation of the focusing ring 63 will cause a change of the distance between the imaging optical system 6 encased in the lens barrel 58 and the CCD 16 housed in the TV camera head 65, allowing a focusing adjustment to be made. The focusing ring 63 is constrained by a focusing ring holder 84 so that its position is not shifted.

In the apparatus of the first embodiment, as mentioned above, the lens barrel 58 is hermetically sealed and thus the TV photographic adapter 64 can be treated by autoclaving. Similarly, the TV camera head 65, which is also hermetically sealed by the sapphire glass cover 62, can be treated by autoclaving. Further, in order to change the magnification for observation of the endoscope image, it is merely necessary to replace the TV photographic adapter 64 with another having an optical system of a different magnification from the imaging optical system 6. The magnification for observation of the endoscope image can thus be varied with great ease.

In order that the lens barrel 58 is fully hermetically sealed by the sapphire glass covers 62, it is desirable that a metallic frame is attached to each of the glass covers 62 and is soldered to the lens barrel 58.

Second Embodiment

Figure 13A:
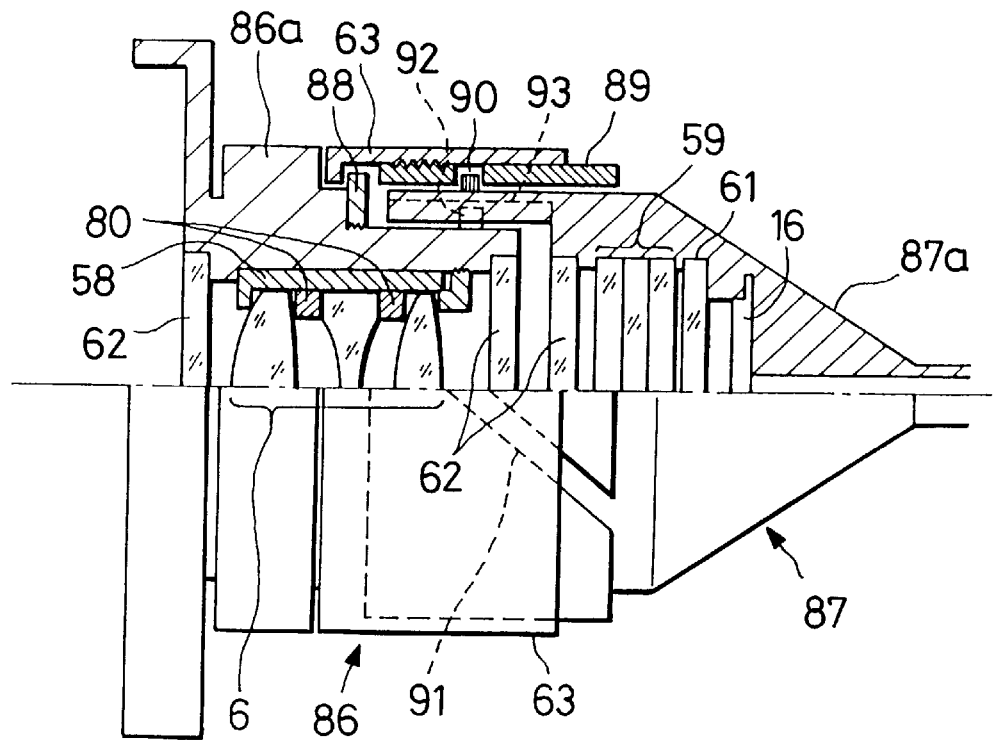
FIGS. 13A, 13B, and 13C are views for explaining the structure and focusing operation of a second embodiment.

The imaging apparatus for endoscopes of this embodiment, as shown in FIG. 13A, is such that a TV photographic adapter 86 is constructed integral with a TV camera head 87. The TV photographic adapter 86 housing the lens barrel 58 in which the imaging optical system 6 is encased is hermetically sealed by the sapphire glass covers 62. Furthermore, the TV photographic adapter 86 is designed so that it can be rotated about the optical axis as its center by the focusing ring 63 and is not separated from the TV camera head 87 by a focusing ring holder 88 attached to an outer frame 86a of the TV photographic adapter 86. The focusing ring 63 has a cam frame 89 fixed thereto.

The TV camera head 87 which is hermetically sealed by the sapphire glass cover 62, on the other hand, is such that an outer frame 87a thereof is provided with a cam pin 90, which is slidably engaged with a cam groove 91 shaped by the focusing ring 63 and the cam frame 89. The outer frame 86a of the TV photographic adapter 86 has a key 92 and the outer frame 87a of the TV camera head 87 has a keyway 93 so that they can be engaged with each other. The TV photographic adapter 86 and the TV camera head 87 are thus constrained to operate along the optical axis only.

Figure 13B:
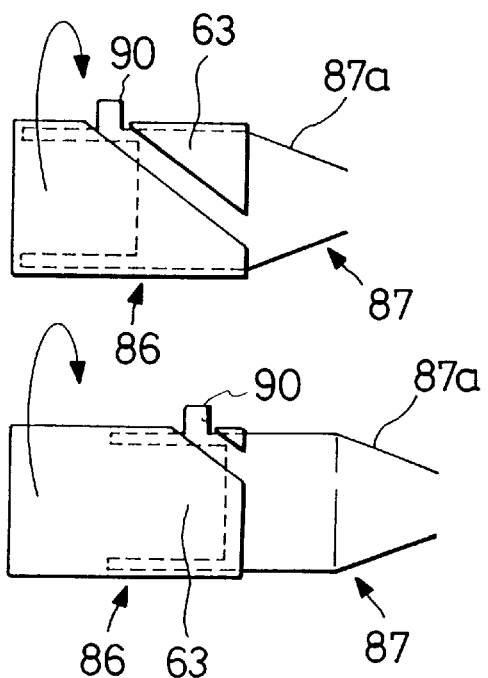
Figure 13C:
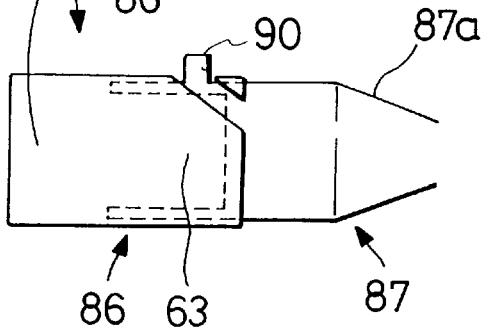

Hence, as shown in FIGS. 13B and 13C, a rotation of the focusing ring 63 about the optical axis will cause the distance between the TV photographic adapter 86 and the TV camera head 87 to change in association with the cam. Consequently, the focusing adjustment becomes possible and the image transmitted from the endoscope, not shown, can be prevented from rotating.

In the apparatus of the second embodiment, as mentioned above, the lens barrel 58 is hermetically sealed and thus the TV photographic adapter 86 can be treated by autoclaving. Similarly, the TV camera head 87, which is also hermetically sealed by the sapphire glass cover 62, can be treated by autoclaving. Further, in order to change the magnification for observation of the endoscope image, it is merely necessary to replace the TV photographic adapter 86 with another having an optical system of a different magnification from the imaging optical system 6. The magnification for observation of the endoscope image can thus be varied with great ease.

In order that the lens barrel 58 is fully hermetically sealed by the sapphire glass covers 62, it is desirable that a metallic frame is attached to each of the glass covers 62 and is soldered to the outer frame 86a of the TV photographic adapter 86.

Figure 1:
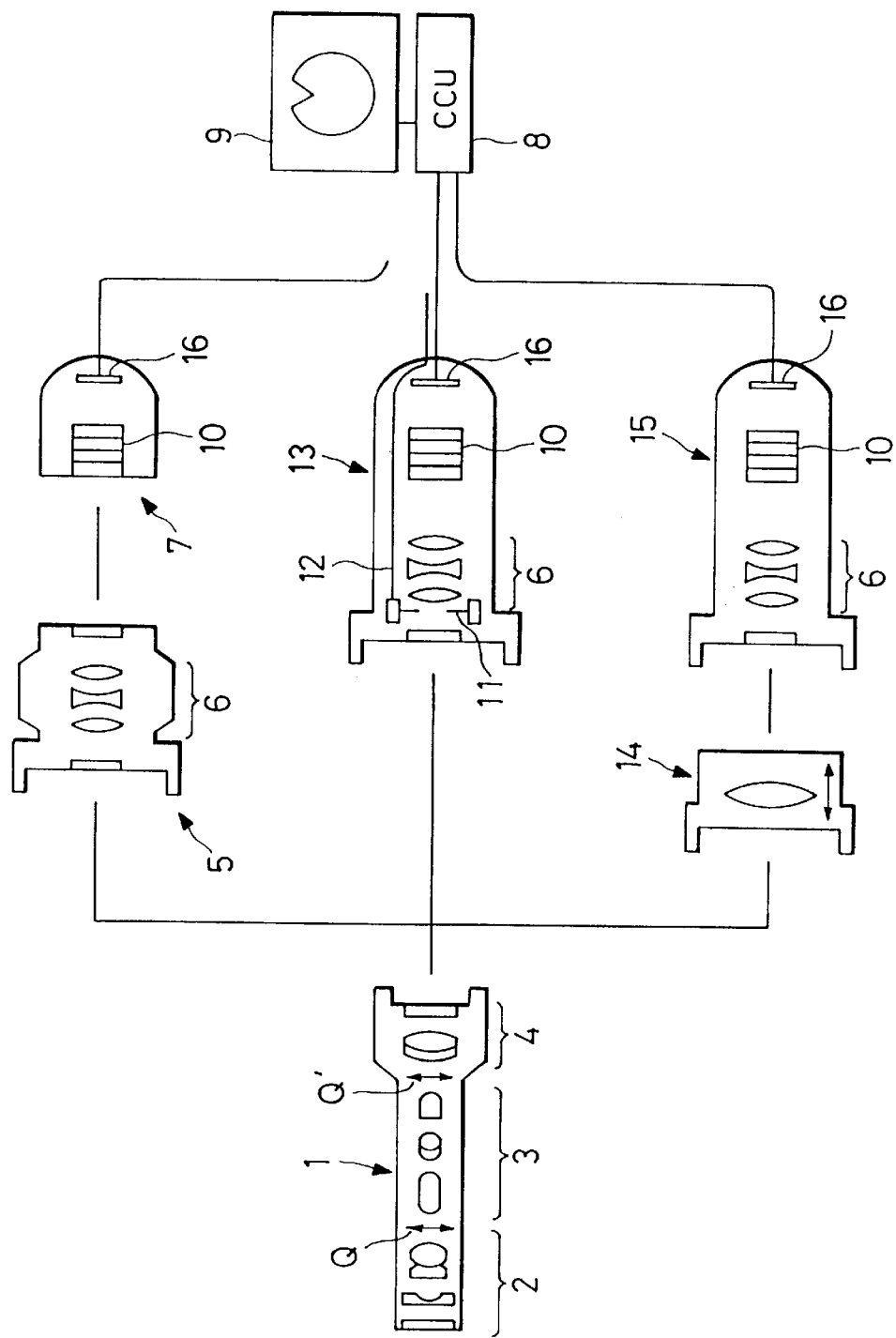
FIG. 1 is a chart for explaining a systematic construction of an endoscope in a conventional imaging apparatus for endoscopes.
Figure 14:
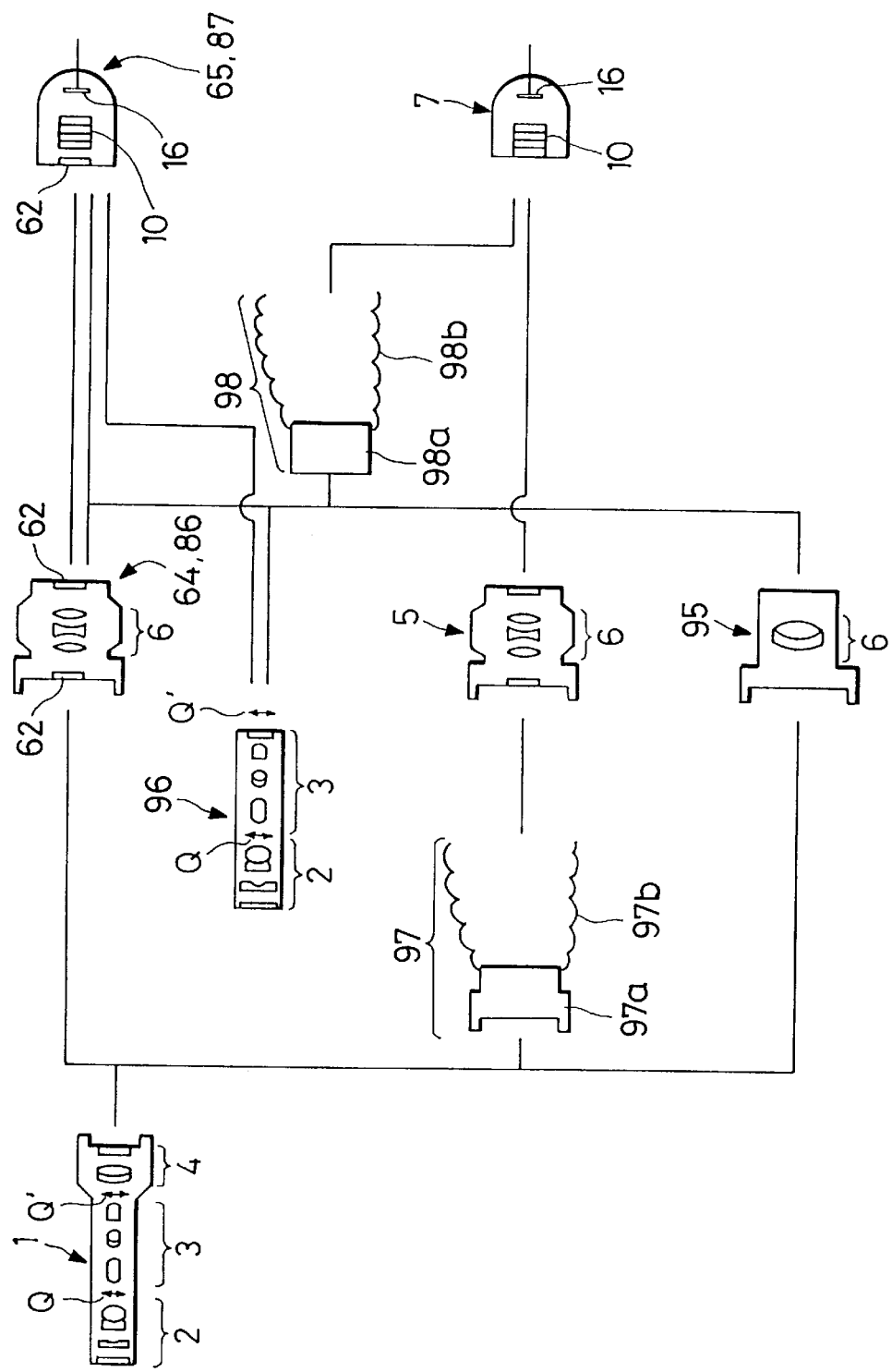
FIG. 14 is a chart for explaining a systematic construction of an endoscope including the imaging apparatus for endoscopes of the present invention.

As described above, the use of the imaging apparatus for endoscopes according to the present invention brings about the system that a user can choose the magnification for observation of the endoscope image at will. In addition to this, the apparatus of the present invention has various merits as follows:

In FIG. 14, the TV photographic adapter 64 or 86 is one used in the imaging apparatus for endoscopes of the present invention. The TV photographic adapter 5 is one used in the conventional apparatus, and a TV photographic adapter 95 is of a throwaway type. The TV camera head 65 or 87 is one used in the Imaging apparatus for endoscopes of the present invention, and the TV camera head 7 is that used in the conventional apparatus. In this figure, devices connected by solid lines shows possible system constructions. Also, although the TV camera heads 13 and 15 depicted in FIG. 1 are not shown in FIG. 14, they can be included in the chart of FIG. 14.

In FIG. 14, a new endoscope 96 is such that the eyepiece section is removed from the conventional endoscope 1 to make a TV observation only. Specifically, by omitting the function of visual observation to make a TV observation only, the eyepiece 4 is eliminated and low cost is obtained. The new endoscope 96 thus constructed is hermetically sealed so that the autoclaving treatment becomes possible. Even with the new endoscope 96, it is desirable that autoclaving treatment be possible and that the TV camera head 65 (or the TV camera head 87) without the imaging optical system be used for image observation.

In this way, the imaging apparatus for endoscopes of the present invention can be constructed with the new endoscope 96, in which the eyepiece section is removed from the endoscope 1, and the TV camera head 65 (or 87) without the imaging optical system 6. Consequently, a reduction in cost can be obtained and excellent system extension is secured.

In the endoscope system shown in FIG. 14, although each TV camera head having the filter unit 10 is too expensive to use as the TV camera head of the throwaway type, the TV photographic adapter of the throwaway type can be lined up with comparative ease and hence can of course be used in the imaging apparatus for endoscopes of the present invention. The TV photographic adapter of the throwaway type uses a plastic lens and the like to advance a cost reduction, but even with a single plastic lens, if an aperture stop is housed therein and is used in a state to reduce brightness to some extent, an image of good practical use can be obtained. It is, of course, desirable that such an aperture stop is made by a lens frame itself for the reason that the number of parts is decreased.

Figure 15:
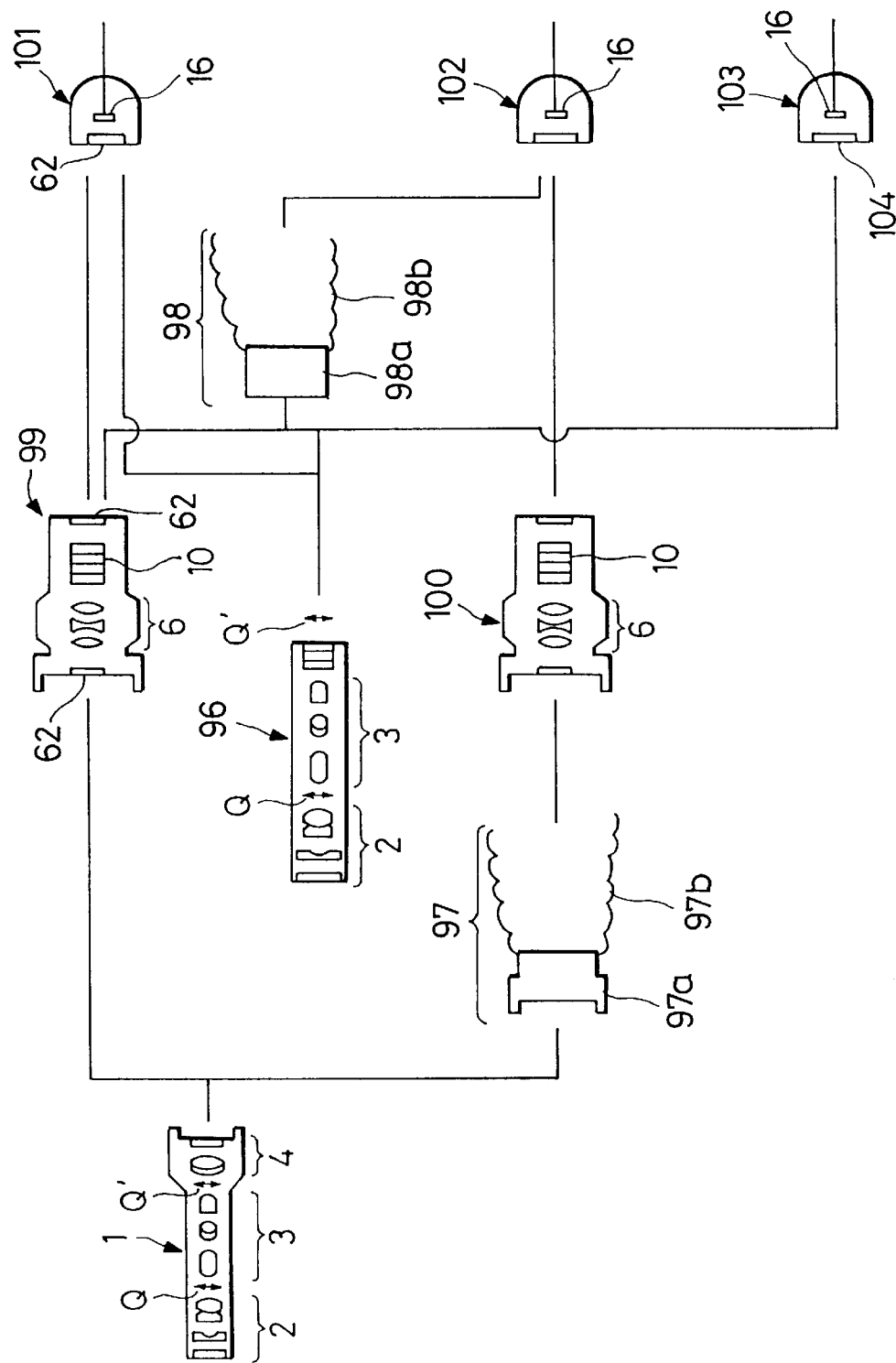

FIG. 15 shows an example of the system construction where the filter unit 10 is removed from each TV camera head shown in FIG. 14 and is incorporated in each TV photographic adapter. The autoclaving resistance is the same as in the system of FIG. 14, and the fact that the filters need not be incorporated in the TV camera head facilitates the use of the TV camera head of throwaway type in the entire system. In a throwaway TV camera head 103, provisions are made to use a plastic cover 104 instead of the glass cover and to incorporate a driver circuit for a CCD drive housed in an ordinary TV camera head in the CCU, not shown, with the intention of bringing about the lowest possible cost because of the property of its product.

In the system shown in the figure, if the plastic cover 104 is configured of material having birefringent properties, the number of plates of the filter unit 10, such as crystal plates, arranged in a TV photographic adapter 99 or 100 will be decreased, and a compact design of the adapter can be obtained. The same is true of TV camera heads 101 and 102. For example, in the TV camera head 101, it becomes possible to add a function as an optical low-pass filter to the sapphire glass cover 62 by properly choosing the orientation of its crystal axis. For the TV camera head 102, it is only necessary to replace the glass cover with the filter unit 10 such as crystal. In each of the TV camera heads 101, 102, and 103, the CCD 16 is situated close to the glass cover and thus, as shown in FIG. 16, if a flare mask 105 for eliminating ghost and flare is placed immediately before the glass cover, a more favorable TV camera head can be constructed.

Moreover, the endoscope system shown in FIG. 15, because there is no need to place filters like crystal in the TV camera head, has the advantage that the back focal distance of the TV camera head can be diminished. In recent years, a ¼-inch CCD has been chiefly used, and the focal length of the imaging optical system 6 used to form an image on this CCD is approximately 10–20 mm. Thus, if the back focal distance is long, a retrofocus lens must be used in the imaging optical system 6. This retrofocus lens, because of its lack of symmetry, has the defect in that the number of lens elements is increased. Where a TV photographic adapter provided with a zoom function, as a system must be designed, it is favorable for the simplification of the above cam structure that the imaging optical system used be constructed with three optical units: a focusing unit, a variator unit, and a compensator unit. However, the use of a retrofocus lens composed of two optical units, which has only the functions of the variator unit and the compensator unit, may cause the complication that the mechanism must have a double structure to perform focusing and zooming operation at the same time.

In general, since an apparatus of such a compli- cated structure is considerably low in strength and is liable to break, it is unfavorable as a design concept that this apparatus be used for surgery.

Also, in order to reduce the back focal distance of the TV camera head, in addition to the above practice, a YAG laser-beam cut-off coating may be applied to the surfaces of the glass covers and lenses of the TV photographic adapter or the TV camera head, or use may be made of an optical low-pass filter instead of the quartz filter, by the scan of the point spread function (which is disclosed, for example, in Japanese Patent Preliminary Publication Nos. Hei 5-80275 and Hei 4-289816). In the system shown in FIG. 15, it is needless to say that the new endoscope 96, which must receive the autoclaving treatment itself, is hermetically sealed by the sapphire glass covers and incorporates optical low-pass filters and infrared cut-off filters therein.

In the endoscope systems shown in FIGS. 14 and 15, a sterilization method for the conventional endoscope system needs to be considered. Hence, sterilized sheaths 97 and 98 are taken into the system, and thereby a system applicable to the conventional imaging apparatus for endoscopes can be provided.

In FIG. 14, the sterilized sheath 97 is composed of a mechanical member 97a connected between the endoscope 1 and the TV photographic adapter 5 and a sterilized bag 97b, in which the TV photographic adapter 5 and the TV camera head 7 are enclosed, and thereby both can be brought into a sanitary region. According to this construction, even though the TV photographic adapter 5 and the TV camera head 7 are not sterilized by gases or wash water, the sterilization treatment can easily be applied. Further, the sterilized sheath 98 is composed of a mechanical member 98a connected between the new endoscope 96 and the TV camera head 7 and a sterilized bag 98b, in which the TV camera head 7 is enclosed, and thereby it can be brought into a sanitary region.

Since each of the mechanical members 97a and 98a is merely composed of a metallic member, it can receive independently the autoclaving treatment. If these members are made of plastic, the sterilized sheaths 97 and 98 can be designed to be disposable. Also, the sterilized sheaths 97 and 98 shown in FIG. 15 are the same as those in FIG. 14.

Each imaging apparatus for endoscopes described above, because it can be treated by autoclaving and does not use the auto-iris device, is manufactured at a relatively low cost and allows the magnification for observation of the endoscope to be easily adjusted, with the result that the system construction having relatively wide extension becomes possible.

In addition to the TV photographic adapter, as mentioned above, in which the user manually performs the focusing operation himself, the imaging apparatus for endoscopes of the present invention is capable of using the TV photographing adapter having the auto-iris device. When the auto-iris device is used, the depth of field is improved by stopping down the stop even though the diopter at the optimum focal length of the endoscope is varied to some extent. Thus, image quality without problems in practical use can be obtained without any focus adjustment. However, where a nearby object is observed in particular, it is necessary to perform the focusing operation. For the imaging apparatus for endoscopes used in this case, the TV camera head 15 shown in FIG. 1 is first considered, but alternatively, for example, a TV photographic adapter 110 shown in FIG. 17 can also be used. The TV photographic adapter 110 includes the auto-iris device 11, a power supply 111 for actuating the auto-iris device 11, a light receiving element 112 for controlling the auto-iris device, and an auto-iris control device 113. Furthermore, this adapter is hermetically sealed through the sapphire glass covers 62 and uses the same mechanism as the TV photographic adapter used in the apparatus of the second embodiment so that focusing becomes possible. By using the TV photographic adapter 110 thus constructed, the autoclaving treatment becomes possible, the auto-iris device can be actuated, and the focusing operation can also be performed.

Besides the TV photographic adapter 110, a TV camera head 115 shown in FIG. 18 may be used as the imaging apparatus for endoscopes of the present invention. The TV camera head 115 is hermetically sealed through the sapphire glass cover 62, and includes the auto-iris device 11, the auto-iris control device 113, the power supply 111, the CCU 8, and an image transmitting section 116 for converting image information into a radio wave to transmit the image, so that a wireless TV camera head for endoscopes is realized. It is needless to say that the TV camera head 115 constructed as mentioned above is unsurpassed in autoclaving treatment.

Although the imaging apparatus for endoscopes of the present invention is constructed as so far explained and thereby can be manufactured at a considerably low cost, a structure for allowing a further reduction in cost will be described below.

FIG. 19 shows the arrangement of a filter unit, such as crystal, housed in the TV photographic adapter or the TV camera head of the imaging apparatus for endoscopes of the present invention. In this figure, reference numeral 117 denotes a filter frame and 118 denotes a filter holder. It is common practice that the filter elements of the conventional filter unit are closely arranged in such a way that an infrared cut-off filter of poor moisture resistance is sandwiched between crystal filters. Such an arrangement, however, has a problem of high cost because a cementing process is required. According to the arrangement shown in FIG. 19, all of the crystal filters 10, the infrared cut-off filter 61, and the YAG laser-beam cut-off filter 60 are arranged with a drop-in structure and are fixed by the filter holder 118, and hence the cementing process of the filters is omitted and a reduction in cost can be obtained. The infrared cut-off filter 61 used here must have high moisture resistance to some extent. The filter holder 118 may be partially cemented with an adhesive. Further, the infrared cut-off filter 61 and the YAG laser-beam cut-off filter 60 may be arranged in reverse order.

In the conventional TV camera head, the positional adjustment of the CCD (that is, moving the CCD along the optical axis to adjust it to the image position) has been in general made at the manufacturing stage, but if an allowance for focus adjustment is set to a slightly larger extent, the process of the positional adjustment of the CCD can be omitted. Moreover, if all the optical systems incorporated in the imaging apparatus for endoscopes so far explained are constructed of plastic, a further reduction in cost can be secured.

In this way, the reduction of the cost relative to the optical system is of great worth as such, but in order to lower the cost of the entire apparatus, it is desirable to eliminate unnecessary parts in mechanical and electrical systems, as well as in the optical system. Thus, for example, the circuit of the electrical system can be eliminated by such construction as described blow.

In recent years, electric light control means, usually called an electronic shutter, has come into prominent use. Reference is now made to the operating conception of the electronic shutter.

FIGS. 20A and 20B are schematic views of the photoelectric converting surface of the CCD of the interline system. As shown in FIG. 20A, square photodiodes 120 are arrayed longitudinally and laterally, and one array in a lateral (horizontal) direction corresponds to one line. As shown in FIG. 20B, a vertical (V) CCD shift register 121 is provided, adjacent to each row of the arrayed photodiodes 120, In a longitudinal direction, and at its output terminal, a horizontal (H) shift register 122 is laterally provided. These shift registers of the CCD are analog shift registers, which serve to output electric charges one after another in synchronization with given driving pulses.

Each of the photodiodes 120 is provided with a charge-storage portion, not shown, so that a photoelectric charge generated can be stored therein. A charge transfer gate 123 is placed between the charge-storage portion and the V CCD shift register 121. When charge transfer pulses are given at once for one field, all photoelectric charges are simultaneously shifted through the charge transfer gate 123 to the V CCD shift register 121. Whenever vertical driving pulses (V pulses) are given at once for one line at the V CCD shift register 121, the photoelectric charges are simultaneously passed upward for one line. The H shift register 122 is located at the place where the photoelectric charges are transferred, so that whenever horizontal driving pulses (H pulses) are given, each of the photoelectric charges is passed sideway (to the left of the figure) for one pixel, and after being converted into a voltage signal by an output amplifier, not shown, is output. In this way, the information of individual pixels is continuously read out from the top left to the bottom right of the image surface and is output as video signals for one field.

For the electric light control means other than the above description, an auto-gain control (hereinafter abbreviated to AGC) function may be used when brightness is insufficient. This AGC is briefly explained below. The video signal output from the CCD, after sample-holding and smoothing, is amplified by the amplifier. In this case, the brightness of the image displayed is adjusted by the setting of the gain (amplification). A circuit for brightness adjustment by the gain is the AGC.

Here, the CCD of an NTSC system stores the electric charges in 1/60 (sec) and transmits the resulting signals. to the V CCD shift register 121. If, however, the time for charge storage is set at 1/30 (sec), the brightness of the image can be improved, and hence even though the AGC circuit is eliminated, the image with sufficient brightness can be provided. As such, cost reduction can be brought about only for the elimination of the AGC circuit. In addition, the cost can be lowered by a combination of the electrical system with the optical system. If, for example, the infrared cut-off filter is removed which is housed in the TV photographic adapter of the imaging apparatus for is removed, the cost will be materially reduced. In this case, however, any image available assumes reddish color, and thus if the color balance is set to blue, the color harmony of the entire image can be maintained.

By devising the structure of the CCD used in the TV camera head of the imaging apparatus for endoscopes of the present invention, a TV camera head capable of favorably correcting chromatic aberration can be realized. FIGS. 21A, 21B, and 21C are schematic views showing the imaging surfaces, cut perpendicularly, of the CCD capable of favorably correcting chromatic aberration. Such a CCD, as shown in FIG. 21A, is provided with a blue (B) filter 125, a green (G) filter 126, and a red (R) filter 127, which are color filters of a primary color system for separating color signals, between the surfaces of macro lenses 128 and photoelectric surfaces 129. In this way, an optical path length to each photoelectric surface 129 corresponding to each filter is set to increase in going from the blue filter to the red filter. Hence, even though chromatic aberration is produced in the imaging optical system placed in the TV photographic adapter or in the CCD placed in the TV camera head of the imaging apparatus for endoscopes of the present invention, focus positions relative to respective colors are made constant to thereby correct such chromatic aberration.

Alternatively, such an effect, as shown in FIG. 21B, is secured by changing the heights of the micro lenses 128 corresponding to individual color filters or, as shown in FIG. 21C, is achieved by providing media n1, n2, and n3 in optical paths lying behind the color filters to change the optical path lengths in terms of air.

The use of the CCD constructed as mentioned above makes it possible to obtain good image quality even where chromatic aberration is yielded in the imaging optical system or the CCD. Thus, the imaging optical system can be constructed with a single lens, and a further reduction in cost is effectively secured.

Also, although in FIGS. 21A–21C the filters 125–127 appear to be arrayed in a line, they are actually arrayed two-dimensionally as shown in FIG. 22. In this figure, a luminance signal Y is obtained from the color element G, and a color difference signal is produced by a difference signal (for example, the value of the color element R—the color element G or the color element B—the color element G) in a direction perpendicular to a field a (a1, a2, . . . ) or a field b (b1, b2, . . . ). The array of the filters shown in FIG. 22 is characterized in that primary colors are used for the color filters and the number of red filters is made small, compared with an ordinary single color CCD for complementary color TV cameras. This is because most of objects in the human body have a red color and thus it is not necessary for the CCD used in the endoscope to have the array of filters sensitive to red color.

In order to exclude an adverse influence brought about when a laser, such as that of YAG, is used, various laser-beam cut-off filters, in addition to the filters 59 and 61, are required for arrangement.

In recent years, since even with a laser device for operation the apparatus using a semiconductor laser requires compact and high-output design, cases not unfrequently occur in which it is desirable to provide filters capable of removing wavelengths of the semiconductor device. These wavelengths are in the range of about 810–1000 nm, depending upon the property of a semiconductor device used. Hence, where such filters are used in combination with the YAG laser-beam cut-off filter (YAG laser wavelength 1060 nm), it is favorable to possess the property of removing wavelengths more than 810 nm in order to attain the compactness of the apparatus and reduce the number of parts. The infrared cut-off filter placed in the TV photographic adapter of the. apparatus may be designed to have the property of removing the wavelengths more than 810 nm. Moreover, it is possible that these filters or the imaging optical system housed in the TV photographic adapter is coated with interference filters to have the above property.

Third Embodiment

FIG. 23 shows the arrangement of an optical system in this embodiment. The final relay image 71, the eyepiece 4, and the glass cover 40 constitute the optical system of the endoscope. The glass cover 42, the auto-iris device 77, and the imaging optical system 6 are the optical system of the TV camera head. The glass covers 40 and 42 are configured of sapphire glass and have water and heat resistance. The focusing lens 74 disposed in the focusing adapter is made of sapphire glass and is designed to perform the focusing operation by changing a distance d. Negative lenses are contained in the imaging optical system 6 of the TV camera head having a watertight structure.

In order to achieve the objects of the present invention, suppress aberrations yielded in lens systems, and realize a compact optical system, it is desirable to satisfy the condition:

$$0.5 < |f_1/f| \tag{1}$$

where f is the compound focal length of the focusing lens 74 and the imaging optical system 6 and $f_1$ is the focal length of the focusing lens 74. It is more desirable to satisfy the condition:

$$0.7 < |f_1/f| < 2 \tag{2}$$

The amount of focus varies with the value of the focal length $f_1$, and if the value of the focal length $f_1$ is too large, the amount of focus will be highly increased and the compactness of the optical system will be lost. Thus, this problem arises when the value of $|f_1/f|$ exceeds the upper limit of Eq. (2) (there is no upper limit where compactness need not be considered). Conversely, if the value of the focal length fi is excessively small, the amount of focus will be reduced and the sensitivity of the optical system to focusing becomes so delicate that the apparatus is hard to use. Furthermore, since the focusing lens 74 is constructed to be independent of the TV camera head, a correction factor for decentering of the focusing lens 74 becomes large, and the eccentricity of the endoscope image comes into question. The use of only a single lens for the focusing lens 74 is unfavorable because strong spherical aberration is produced.

If the value of the focal length $f_1$ is made relatively small, the position of the pupil of the optical system located behind the focusing lens 74 (on the TV camera side) becomes closer to the focusing lens 74. In this case, if the positional shift between the pupil and the auto-iris device 77 is considerable, the vignetting of a marginal beam will be caused when the auto-iris device 77 is stopped down. It is therefore desirable that the value of $|f_1/f|$ is set not to pass the lower limit of Eq. (1) or (2).

Furthermore, the optical system of the third embodiment satisfies Eq. (2) and thereby is made to share an imaging function, to some extent, with the focusing lens 74, so that aberrations (spherical aberration and astigmatism) produced in the eyepiece 4 and the focusing lens 74 are corrected by the imaging optical system 6 in the TV camera head. For this reason, the imaging optical system 6 contains negative lenses. In this way, the optical system is favorably corrected for aberrations.

Since the rigid endoscope requires the amount of focus of at least ±1 diopter, the movement d of the focusing lens 74 must be fully ensured accordingly. It is thus desirable that when a distance from the auto-iris device 77 to the focusing lens 74 (in terms of air) is represented by 1, the following condition is satisfied at the center of the focusing distance:

$$0.1 < |1/f_1| < 0.5 \qquad (3)$$

If the value of $|1/f_1|$ exceeds the upper limit of Eq. (3), the position of the pupil will be largely shifted from that of the auto-iris device 77, thus causing vignetting. Moreover, since the distance between the pupil and the imaging optical system 6 will be increased, the entire optical system becomes large-sized. If, on the other hand, the value of $|1/f_1|$ passes the lower limit of Eq. (3), the amount of focus becomes insufficient.

What follows is the numerical data of the optical system in the third embodiment.

Object distance = −4.89, Magnification = −1.936, f = 10, $f_1$ = 8.825,
$f_2$ (focal length of imaging optical system 6) = 56.882,
$f_1/f$ = 0.8825, $f_1/f_2$ = 0.1551

| Dioper $1/f_1$ | −1 0.1918 | 0 0.1820 | +1 0.1727 |
|---|---|---|---|

| | | | |
|---|---|---|---|
| $r_1$ = 6.3973 | | | |
| | $d_1$ = 0.2709 | $n_1$ = 1.78472 | $v_1$ = 25.71 |
| $r_2$ = 2.4609 | | | |
| | $d_2$ = 0.7827 | $n_2$ = 1.66672 | $v_2$ = 48.32 |
| $r_3$ = −5.6582 | | | |
| | $d_3$ = 1.0205 | | |
| $r_4$ = ∞ | | | |
| | $d_4$ = 0.9031 | $n_4$ = 1.76820 | $v_4$ = 71.79 |

-continued

| | | | |
|---|---|---|---|
| $r_5$ = ∞ | | | |
| | $d_5$ = 0.9633 | | |
| $r_6$ = 5.6839 | | | |
| | $d_6$ = 0.4515 | $n_6$ = 1.76820 | $v_6$ = 71.79 |
| $r_7$ = 33.9537 | | | |
| | $d_7$ = 0.6044 | | |
| $r_8$ = ∞ | | | |
| | $d_8$ = 1.5052 | $n_8$ = 1.76820 | $v_8$ = 71.79 |
| $r_9$ = ∞ | | | |
| | $d_9$ = 0.1505 | | |
| $r_{10}$ = ∞ (auto-iris) | | | |
| | $d_{10}$ = 0.5208 | | |
| $r_{11}$ = 1.5457 | | | |
| | $d_{11}$ = 0.5713 | $n_{11}$ = 1.56873 | $v_{11}$ = 63.16 |
| $r_{12}$ = 2.3295 | | | |
| | $d_{12}$ = 0.7455 | | |
| $r_{13}$ = −3.1395 | | | |
| | $d_{13}$ = 0.5986 | $n_{13}$ = 1.80518 | $v_{13}$ = 25.43 |
| $r_{14}$ = 1.6625 | | | |
| | $d_{14}$ = 0.8894 | | |
| $r_{15}$ = 6.0283 | | | |
| | $d_{15}$ = 0.5870 | $n_{15}$ = 1.80100 | $v_{15}$ = 34.97 |
| $r_{16}$ = −3.5327 | | | |

Fourth Embodiment

FIG. 24 shows the arrangement of an optical system in this embodiment. The optical system of the fourth embodiment is such that the crystal glass lens incorporated in the focusing adapter of the optical system shown in the third embodiment is replaced by another lens having a different focal length to shift the center of the range of the focus adjustment. Although in the optical system of the third embodiment the object point located behind the eyepiece 4 (on the TV camera side) is at a finite distance, that in the optical system of the fourth embodiment is at infinity. Since a focusing lens 74' is disposed similar to the focusing lens 74 of the third embodiment, both lenses have almost the same focusing range, but its center position is different. The distance between the glass covers 40 and 42 is identical with the case of the third embodiment.

In this way, the replacement of the focusing lens brings about a wider focusing range.

The following is the numerical data of the optical system in the fourth embodiment.

Object distance=−4.99, Magnification=−1.920, f = 10.256, $f_1$ = 9.1, $f_2$ = 56.882,
$f_1/f$ = 0.887, $f_1/f_2$ = 0.16, $1/f_1$ = 0.176

| | | | |
|---|---|---|---|
| $r_1$ = 6.3873 | | | |
| | $d_1$ = 0.2709 | $n_1$ = 1.78472 | $v_1$ = 25.71 |
| $r_2$ = 2.4609 | | | |
| | $d_2$ = 0.7827 | $n_2$ = 1.66672 | $v_2$ = 48.32 |
| $r_3$ = −5.6582 | | | |
| | $d_3$ = 1.0205 | | |
| $r_4$ = ∞ | | | |
| | $d_4$ = 0.9031 | $n_4$ = 1.76820 | $v_4$ = 71.79 |
| $r_5$ = ∞ | | | |
| | $d_5$ = 0.9633 | | |
| $r_6$ = 5.7565 | | | |
| | $d_6$ = 0.4515 | $n_6$ = 1.76820 | $v_6$ = 71.79 |
| $r_7$ = 31.4927 | | | |
| | $d_7$ = 0.6044 | | |
| $r_8$ = ∞ | | | |
| | $d_8$ = 1.5052 | $n_8$ = 1.76820 | $v_8$ = 71.79 |
| $r_9$ = ∞ | | | |
| | $d_9$ = 0.1505 | | |
| $r_{10}$ = ∞ (auto-iris) | | | |
| | $d_{10}$ = 0.5208 | | |
| $r_{11}$ = 1.5457 | | | |
| | $d_{11}$ = 0.5713 | $n_{11}$ = 1.56873 | $v_{11}$ = 63.16 |

-continued $$f = 10.256, f_1 = 9.1, f_2 = 56.882,$$
$$f_1/f = 0.887, f_1/f_2 = 0.16, 1/f_1 = 0.176$$

| | | | |
|---|---|---|---|
| $r_{12} = 2.3295$ | | | |
| | $d_{12} = 0.7455$ | | |
| $r_{13} = -3.1395$ | | | |
| | $d_{13} = 0.5986$ | $n_{13} = 1.80518$ | $v_{13} = 25.43$ |
| $r_{14} = 1.6625$ | | | |
| | $d_{14} = 0.8894$ | | |
| $r_{15} = 6.0283$ | | | |
| | $d_{15} = 0.5870$ | $n_{15} = 1.80100$ | $v_{15} = 34.97$ |
| $r_{16} = -3.5327$ | | | |

Fifth Embodiment

FIG. 25 shows the arrangement of an optical system in this embodiment. The optical system of the fifth embodiment is such that the rear lens unit of the optical system shown in the third embodiment is replaced with another. Specifically, the imaging optical system 6 placed in the TV camera head is replaced by an imaging optical system 6'.

Thus, in order to obtain the same advantage even where the focal length of the rear lens unit is changed, the following two points are considered.

(1) Where the image size of the image sensor is changed, it is merely necessary that the user purchases only the TV camera head including the imaging optical system 6' of the rear lens unit.

(2) Where the user makes observations through the endoscope at various magnifications, he can use interchangeably TV camera heads having different focal lengths.

The numerical data of the optical system in the fifth embodiment is shown below.

Object distance = −4.89, Magnification = −1.289, $$f = 6.739, f_1 = 8.825, f_2 = 12.217,$$
$$f_1/f = 1.309, f_1/f_2 = 0.7224$$

| Dioper $1/f_1$ | −1 0.2151 | 0 0.1830 | +1 0.1515 |
|---|---|---|---|
| $r_1 = 6.3873$ | | | |
| | $d_1 = 0.2709$ | $n_1 = 1.78472$ | $v_1 = 25.71$ |
| $r_2 = 2.4609$ | | | |
| | $d_2 = 0.7827$ | $n_2 = 1.66672$ | $v_2 = 48.32$ |
| $r_3 = -5.6582$ | | | |
| | $d_3 = 1.0205$ | | |
| $r_4 = \infty$ | | | |
| | $d_4 = 0.9031$ | $n_4 = 1.76820$ | $v_4 = 71.79$ |
| $r_5 = \infty$ | | | |
| | $d_5 = 0.9633$ | | |
| $r_6 = 5.6839$ | | | |
| | $d_6 = 0.4515$ | $n_6 = 1.76820$ | $v_6 = 71.79$ |
| $r_7 = 33.9537$ | | | |
| | $d_7 = 0.6044$ | | |
| $r_8 = \infty$ | | | |
| | $d_8 = 1.5052$ | $n_8 = 1.76820$ | $v_8 = 71.79$ |
| $r_9 = \infty$ | | | |
| | $d_9 = 0.1505$ | | |
| $r_{10} = \infty$ (auto-iris) | | | |
| | $d_{10} = 0.0301$ | | |
| $r_{11} = 1.4324$ | | | |
| | $d_{11} = 0.5292$ | $n_{11} = 1.56873$ | $v_{11} = 63.16$ |
| $r_{12} = 2.6224$ | | | |
| | $d_{12} = 0.6629$ | | |
| $r_{13} = -5.7150$ | | | |
| | $d_{13} = 0.3010$ | $n_{13} = 1.80518$ | $v_{13} = 25.43$ |
| $r_{14} = 1.2550$ | | | |
| | $d_{14} = 0.7464$ | | |
| $r_{15} = 3.3828$ | | | |
| | $d_{15} = 0.4515$ | $n_{15} = 1.80100$ | $v_{15} = 34.97$ |
| $r_{16} = -3.9884$ | | | |

Sixth Embodiment

FIG. 26 illustrates the structure of the imaging apparatus for endoscopes in this embodiment. The imaging apparatus for endoscopes of the sixth embodiment is used by connecting the TV camera head 45 with the eyepiece section of the endoscope 1. The devices, constituting the imaging apparatus, placed behind the TV camera head 45 are the same as in the prior art, and thus their explanations are omitted here.

The camera head 45 comprises the imaging optical system 6; the stop unit 46 for holding the imaging optical system 6, equipped with the auto-iris device 38; the CCD 16; the filter unit 10 disposed immediately before the CCD 16; a frame member 130 for holding the filter unit 10 and the CCD 16; and the focus adjusting knob 48 attached to the frame member 130. The auto-iris device 38 includes a stop blade portion for changing the size of its aperture and a drive, not shown, for driving the stop blade portion. The glass cover 42 with heat resistance is placed in front of the TV camera head (at the connection with the endoscope 1). Focusing in the imaging apparatus is performed in such a way that the focus adjusting knob 48 is operated to move the CCD 16 along the optical axis with respect to the imaging optical system 6.

In the apparatus of the sixth embodiment, since the imaging optical system 6 is held by the stop unit 46 having the auto-iris device 38, the relative positions of the auto-iris device 38 and the imaging optical system 6 are kept always constant and remain unchanged even in the focusing operation of the imaging optical system 6. Hence, because the height of a ray passing through the imaging optical system 6 remains constant even before and after the focusing operation, it is not necessary to consider the balance of variation for aberration of the imaging optical system 6 in the focusing operation, and an always good image is obtained.

Moreover, the imaging optical system 6 is held by the double frame structure of the outer frame 45a of the TV camera head 45 and the stop unit 46, and hence the outside diameter of the TV camera head 45 can be diminished compared with the conventional triple frame structure. There is little fear of causing the decentering of the imaging optical system 6 by clearance between mutual frames. Since the outside diameter of the lens unit constituting the imaging optical system 6 can be taken as the maximum allowable outside diameter of the TV camera head 45, the amount of marginal light of the lens can be reduced, and the amount of light striking the lens frame (stop unit 46) which causes ghost and flare can also be reduced.

The apparatus of the sixth embodiment, as depicted in FIG. 27, may be designed so that the CCD 16 and the filter unit 10 are fixed in the TV camera head 45 and the stop unit 46 is equipped with the focus adjusting knob 48, which is operated to move the imaging optical system 6, together with the stop unit 46, along the optical axis with respect to the CCD 16, thereby performing the focusing operation. In this case also, the same effect as in the apparatus shown in FIG. 26 can be secured.

In order to avoid the reduction of the amount of marginal light as far as possible and suppress variation for aberration due to focusing and decentering caused by clearance between mutual frames or the frame and the lens, it is only necessary to make the position of the auto-iris device 38 coincide with that of the exit pupil of the endoscope 1. It is therefore favorable that the auto-iris device 38 is place ahead of the imaging optical system 6. Specifically, in the apparatus of the sixth embodiment, as shown in FIGS. 26 and 27, it is the best practice that an arrangement is made in the order of the final image Q' of the relay system of the endoscope 1, the objective lens 4, the auto-iris device 38, the imaging optical system 6, and the CCD 6.

Where the TV camera head 45 is designed to have the auto-iris function as in the sixth embodiment, the aperture size of the auto-iris device is adjusted according to the brightness of the endoscope image available during the use of the imagingapparatus for endoscopes. Thus, although the apparatus has the focusing function, it extremely diminishes in frequency of actual focusing. Basically, if a focus position is determined once, a further focusing operation will not be required. It follows from this that a principal role of the focusing function is to correct the variation of focus in accordance with an endoscope mounted to the TV camera head. 45 (its detail will be described later). Under these circumstances, on the other hand, the possession of the focus adjusting knob, shown in FIGS. 26 and 27, capable of analogically changing the focus position at will makes the use of the apparatus inconvenient.

In an endoscope, notably in a rigid endoscope, many lenses are arranged from the objective lens to the eyepiece, and the position of the object which must be brought into a focus may be somewhat shifted because of the manufacturing and assembly errors of individual lenses. In FIG. 28A, light from a point P is transmitted through the objective lens and the relay lens of the rigid endoscope 1 and emerges as a parallel beam from the eyepiece (diopter 0 $m^{-1}$). In FIG. 28B, on the other hand, light from a point P' is sent by the objective lens and the relay lens of an endoscope 1' and emerges as a parallel beam from the eyepiece. Where the parallel beam is imaged on the CCD by the TV camera head mounted to the eyepiece of the rigid endoscope, the image of the object located at the point P in the endoscope 1 shown in FIG. 28A or at the point P' in the endoscope 1' shown in FIG. 28B is most clearly observed. Specifically, the position of the most clearly imaged object varies with the individual endoscope. This is the variation of focus caused by products. Focusing for correcting the variation of focus described here is that adjustment is made (the position of the CCD is shifted) so that the image of the object is most clearly formed at the point P in any endoscope.

In general, the difference in focusing between the camera and the endoscope is as follows:

Focusing usually called is performed for the purpose of following the change of the object position. In the endoscope, however, the depth of field is very large, and, for example, in the endoscope 1 shown in FIG. 28A, any object lying in a range indicated by arrows can be very sharply captured. Hence, the endoscope 1 constructed in a favorable state does not require the focusing function. The rigid endoscope is used not for photographing from a considerably distant object to a nearby object as in a camera, but for observing particular parts lying inside human internals or machines. Thus, all objects to be observed exist in the depth of field, and the focusing operation performed in a common camera is unnecessary.

The depth of field changes with the aperture size of the stop, and if the stop is stopped down, the depth of field becomes large. If the depth of field is extremely increased, the positional shift, such as that between the points P and P', will not offer any problem. In actual practice, if the aperture size of the stop is made too small, the image obtained becomes dark, and hence there is a limit to the increase of the depth of field. In FIGS. 28A and 28B, since the region of overlapping of the depths of field is small, the ranges in which the object is clearly viewed are different and a problem arises. Where this is corrected, the size of the stop is diminished and thereby both the functions of increasing the depth of field and moving the CCD along the optical axis to change a light-receiving position are usable. Consequently, the CCD can be roughly moved, to some extent, for its positioning. Thus, it is only necessary to provide a mechanism for making adjustment so that discontinuous or sporadical objects are brought into focus. This rather facilitates the use of the apparatus.

If variations in the focus of the rigid endoscope are in the range of ±0.5 $m^{-1}$, the rigid endoscope can be satisfactorily applied by using the auto-iris device, and any rigid endoscope can dispense with the need for focusing. Beyond this range, the focusing operation is required. Specifically, in the apparatus shown in FIG. 27, when the focal length of the imaging optical system 6 is denoted by f, the amount of movement for focusing of the imaging optical system 6 per $m^{-1}$ is $f^2/1000$, and it is the best practice to provide a stepping focus adjusting mechanism for performing the focusing operation once every $f^2/1000$. Moreover, variations in the focus of each rigid endoscope are up to ±1 $m^{-1}$, and thus the focus adjusting mechanism mounted in the TV camera head which is constructed from dial type design, such as that shown in FIG. 29A, is very convenient for use.

In the vicinity of a dial 135 shown in FIG. 29A, indicators 136a, 136b, and 136c are provided in increments of 1 $m^{-1}$. If the indicators 136a–136c are provided at the positions of at least ±1 $m^{-1}$ with respect to the focus position in a standard condition, it is quite possible to accommodate variations in the focus of the rigid endoscope. In this case, it is desirable that at least three indicators are provided. Also, this dial type focus adjusting mechanism, as shown in FIG. 29B, is mounted on the side of the TV camera head 45. By rotating the dial 135, the CCD 16, in the apparatus shown in FIG. 26, or the imaging optical system 6, in FIG. 27, can be moved along the optical axis.

For the TV camera head equipped with such a dial type focus adjusting mechanism, it is only necessary that when the endoscope is mounted, the dial is set once to the position of any indicator to determine a rough focus position. After that, the focus adjustment is made by merely actuating the auto-iris device attached to the apparatus, and hence such focusing operation as already mentioned is not required. Also, because there is the fear that a focus deviates during the use of the rigid endoscope, it is more effective that the dial is provided with a click mechanism or fixed by a fixed screw after the focus adjustment.

Seventh Embodiment

In the case of an endoscope for medicine, a thorough sterilization treatment of the endoscope after use is indispensable for the prevention of an infectious disease. Although in the past the sterilization treatment, as previously described, has been made by a gas, such as EOG, and wash water, sterilization gases are virulent as well known, and in order to ensure the safety of sterilization work, the work becomes complicated. Furthermore, there is the problem that waste treatment of the wash water is expensive. In recent years, therefore, a heat sterilization (autoclaving) method which is not attended with the complicated work is being chiefly used in the sterilization work of the endoscope apparatus.

However, for example, in the attachment TV camera which is removably mounted to the eyepiece section of the endoscope to form the endoscope image, watertight properties are sufficient for ordinary use, but it is difficult to completely seal the camera under the conditions of high temperature and pressure in the autoclaving treatment. Thus, steam is admitted into the camera and tarnish develops in the optical system. Moreover, for electronic parts provided in the TV camera, degradation and corrosion may be caused.

In the apparatus for which the autoclaving treatment is made, it is impossible that, as have been done in the past, a knob is provided outside the TV camera head to manually move the imaging optical system.

Thus, in the imaging apparatus for endoscopes of the seventh embodiment, the auto-iris device is mounted to perform an optimum focusing operation and at the same time, the sterilization treatment is made possible.

Specifically, the apparatus of the seventh embodiment includes a TV photographic adapter which is removably mounted to the eyepiece section of the endoscope, having lens members for changing the degree of convergence or divergence of a light beam emerging from the eyepiece section; and a watertight camera which is removably mounted to the adapter, having an image sensor therein, so that when the camera is mounted through the adapter to the eyepiece section of the endoscope, the distance between the adapter and the camera is changed and thereby the focusing operation is performed.

In the apparatus of the seventh embodiment, Instead of the adapter, a plurality of adapters each housing a lens unit with a different focal length can be used, and the lens unit can also be constructed with a single lens. Furthermore, the adapter is equipped with a stop (auto-iris device) whose aperture size is variable.

The seventh embodiment is specifically explained below. FIG. 30 shows the case where the endoscope (rigid endoscope) 1 is mounted to the TV photographic adapter 25 and the TV camera head 27 which have autoclaving resistance. The endoscope 1 is the same as the conventional one. The apparatus of the seventh embodiment is such that the final image Q' transmitted by the image transmission system of the endoscope 1, after passing through the eyepiece 4 and the glass cover 40, is formed on the CCD 16 through the imaging optical system 6 supported by the stop unit 46 having the auto-iris device 38. The connection between the TV photographic adapter 25 and the eyepiece section of the endoscope 1 is constructed so that both can be relatively rotated about the optical axis. Further, the connection between the TV photographic adapter 25 and the TV camera head 27 is formed with screws 139 and 140, respectively. In this way, when the TV photographic adapter 25 is rotated about the optical axis, the TV camera head is moved back and forth along the optical axis accordingly. The distance between the TV photographic adapter 25 and the TV camera head 27 is thus changed and the focusing operation can be performed.

Since both the TV photographic adapter 25 and the TV camera head 27 require watertight compartments sufficient for autoclaving resistance, the glass covers 42 having autoclaving resistance divide the imaging optical system 6 from the filter unit 10 and the CCD 16. In order to have heat resistance to the autoclaving treatment, it is desirable that the glass cover 42 is made not of an ordinary optical member, but of crystal glass, such as sapphire, quartz, and rock crystal.

In this way, the attachment TV camera head mounted to the endoscope 1 can have the auto-iris device and autoclaving resistance. Of course, it is suggested that the TV photographic adapter 25 and the TV camera head 27 are used as throwaway units. In this case, the glass covers 42 becomes unnecessary.

The TV photographic adapter 25 may be provided with crystal glass having autoclaving resistance, instead of the glass covers 42, placed before and behind the stop unit 46 so that the imaging optical system 6 is enclosed. The placement of such crystal glass makes it possible to suppress the production of chromatic aberration to some extent.

In general, where the auto-iris devices are manufactured, various errors are caused, to some extent, to respective products even with the same specification. Specifically, sizes of the maximum and minimum diameters of the auto-iris devices vary with products. Here, reference is made to conditions to be satisfied when the aperture size of the auto-iris device is changed to increase the depth of field in the imaging apparatus for endoscopes of the present invention.

If one definer $\phi_2$ as the minimum limit value of the aperture diameter of the auto-iris device, F the focal length of the optical system, and Px the pixel pitch in the horizontal scanning direction of the CCD, it is desirable that the imaging apparatus for endoscopes of the present invention satisfies the condition:

$$\phi_2 \geq 2.15 \times 10^{-4} F/Px \tag{4}$$

In the imaging apparatus for endoscopes, if the aperture diameter of the auto-iris device is made extremely small, a reduction in resolving power will be caused by the diffraction limit of light, and the depth of field cannot be improved even through the auto-iris device is stopped down. Thus, in order to avoid such a problem, it is necessary to define the above condition which is optimum for the endoscope. This condition can be found as follows:

The above condition, where the aperture diameter of the auto-iris device is diminished, is defined in view of the balance between a pan-focus effect by which the depth of field is increased and a reduction of the resolving power by the diffraction limit of light in the auto-iris device.

It is assumed that a color filter, such as that shown in FIG. 31, is placed on the surface of the CCD. Individual filter elements of the color filter are provided corresponding to individual pixels which give rise to photoelectric conversion, and are represented by G for green, Mg for magenta, C for cyan, and Y for yellow. Since the CCD reads out two pixels as one unit in a horizontal direction, a Nyquist rate fn is given by $$fn = 1/(2\ Px) \tag{5}$$

In a TV photographic optical system using the CCD, since an optical low-pass filter for eliminating moire is in general disposed, there is a need to consider the frequency characteristic of the entire optical system, including this filter. Where the Nyquist rate is given by Eq. (5), in view of the use of a TV camera attached to the eyepiece section of the endoscope, the optical low-pass filter disposed in the photographic optical system is desirable to have the frequency characteristics such as those shown in FIG. 32. In this figure, the axis of abscissas is a spatial frequency fr (unit: line/mm) and the axis of ordinates is a spatial frequency response represented by MTF (modulation transfer function). A solid curve α represents the spatial frequency characteristic of the optical low-pass filter, and a broken curve β represents the frequency characteristic of the optical system excluding the optical low-pass filter. Although the optical low-pass filter has the characteristic that the response becomes zero on the somewhat low frequency side of the Nyquist frequency fn, a spatial frequency fn' at which the MTF is at least 30%, in terms of the Nyquist frequency fn of the CCD, becomes $$fn' \div 0.6\ fn \tag{6}$$

This frequency is an effective resolution limit of the CCD.

In contrast to this, the frequency response of the optical system excluding the filter varies with the aperture diameter of the stop, and a diffraction limit (Rayleigh's limit) frequency fa with the optical system is given by $$fa = 1/(1.22\lambda F_{NO}) = 1395\phi/F \quad (7)$$

where $\lambda = 587.56$ nm, $F_{NO} = F/\phi$, and $\phi$ is the aperture of the auto-iris device.

Here, although it is required that the aperture $\phi$ of the auto-iris device corresponding to the F-number is actually calculated with an effective F-number, a general diopter of the rigid endoscope is about $-1$ (m$^{-1}$), and therefore, the object distance regarding the photographic optical system is in the neighborhood of 1000 mm. Since the focal length F of the TV photographic optical system for endoscopes is nearly 10–50 mm, the object distance may be considered to be practically infinite, and the effective F-number may be regarded as about equal to the F-number.

The diffraction limit frequency becomes low as the aperture size of the auto-iris device is diminished, and the broken curve $\beta$ shown in FIG. 32 is moved to the left of the figure. Subsequently, when the broken curve $\beta$ is shifted to the left of the solid curve $\alpha$, the blurring of the image caused by diffraction becomes prominent. In order to obviate this blurring, it is desirable to satisfy the condition:

$$fn \leq fa \quad (8)$$

The substitution of Eqs. (5) and (7) in Eq. (8) gives the condition of Eq. (4). If the value of the aperture $\phi_2$ is below the lower limit of Eq. (4), the degradation of the resolving power will be produced by the influence of diffraction as mentioned above, and the effect of improvement of the depth of field secured by stopping down the stop will not be achieved. However, in the case of the endoscope for medicine, the inside of the human body is observed and thus the degradation of the resolving power by the influence of diffraction is hard to feel beyond an observer's expectation. Hence, for Eq. (6), the following condition is satisfactory:

$$fn' \div 0.42\, fn \quad (6')$$

The reflection of Eq. (6') in Eq. (4) gives $$\phi_2 \geq 1.5 \times 10^{-4} F/Px \quad (9)$$

Although it has been shown that for the optimum range of the minimum aperture diameter of the auto-iris device, its lower limit value as the minimum limit value $\phi_2$ is specified by Eq. (4) or (9), its upper limit value is found as follows:

FIG. 33 shows the relation between an imaging position I and the position of an imaging plane P in the endoscope. A focal depth $\Delta SK$ in this case is expressed by $$\Delta SK = d\, F_{NO} = d\, F/\phi_2 \quad (10)$$

where d is the diameter of the circle of confusion. Eq. (10) is rewritten as $$\phi_2 = d\, F\, 1/\Delta SK \quad (10')$$

Here, in order to bring the above focus state to a stepping focus every 1 m$^{-1}$, it is favorable that the focal depth $\Delta SK$ satisfies the condition:

$$\Delta SK \geq (1/2)F^2/1000 \quad (11)$$

The relation between the diameter d of the circle of confusion and a spatial frequency Uc for allowing resolution in the optical system is given by $$Uc = 1.22/d \quad (12)$$

In the present invention, Uc=Um (a Nyquist limit rate of the image sensor), and thus when Eq. (5) is used, the diameter is expressed as $$d = 1.22/Um = 2.44\, Px \quad (13)$$

Hence, from Eqs. (10), (11), and (13), the following condition is introduced:

$$\phi_2 \leq 4.88 \times 10^{-3}\, Px/F \quad (14)$$

Actually, it is necessary only that Eq. (11) is satisfied the condition:

$$\Delta SK \geq (1/3)F^2/1000 \quad (15)$$

As a result, the upper limit value of the minimum aperture diameter of the auto-iris device becomes $$\phi_2 \leq 7.32 \times 10^{-3}\, Px/F \quad (16)$$

Thus, if Eq. (9) is combined with Eq. (16), the optimum range of the minimum limit value $\phi_2$ of the aperture diameter of the auto-iris device can be found. That is, the range of the minimum limit value $\phi_2$ becomes $$1.5 \times 10^{-4}\, F/Px \leq \phi_2 \leq 7.32 \times 10^{-3}\, Px/F \quad (17)$$

where $\phi_2$ is in millimeters.

Also, the apparatus of the present invention has been explained on the premise that the stop used is variable (auto-iris), but if brightness is amply sufficient, a fixed aperture stop may be incorporated in the TV camera head or the TV photographic adapter.

According to the present invention, as mentioned above, the imaging apparatus for endoscopes can be realized in which the auto-iris device is used in the attachment TV camera for endoscopes, and thereby optimum brightness of the object image is always maintained to optimize the effect of stopping down the stop of the auto-iris device, in a pan-focus state making the burden light for a user and without producing the degradation of the resolving power by the diffraction limit.

Eighth Embodiment

This embodiment assumes the apparatus having the attachment TV camera for endoscopes in which the auto-iris device satisfying the above conditions is mounted. The apparatus of the eighth embodiment, as shown in FIG. 34, includes, in order from the eyepiece side of the endoscope, not shown, the glass cover 42, the auto-iris device 38, the imaging optical system 6, the filter unit 10, the glass cover 42, and the CCD 16. The auto-iris device 38 and the imaging optical system 6 are fixed to the stop unit, not shown. The object image is incident from the eyepiece optical system of the endoscope, not shown, through the glass cover 42 and the auto-iris device 38 on the imaging optical system 6, and is formed through the filter unit 10 and the glass cover 42 on the imaging surface of the CCD 16.

What follows is the numerical data of the optical members, such as lenses, housed in the TV camera head used in the apparatus of the present invention. Focal length f of imaging optical system 6=18.9 mm Pixel pitch in the horizontal scanning direction of CCD 16=4.75 μm Minimum limit value $\phi_2$ of the aperture diameter of auto-iris device 38: $0.567 \leq \phi_2 \leq 1.84$

| | | | |
|---|---|---|---|
| $r_1 = \infty$ | | | |
| | $d_1 = 0.7000$ | $n_1 = 1.51633$ | $v_1 = 64.15$ |
| $r_2 = \infty$ | | | |
| | $d_2 = 10.1000$ | $n_2 = 1.77250$ | $v_2 = 49.60$ |
| $r_3 = \infty$ | | | |
| | $d_3 = 1.0000$ | $n_3 = 1.56384$ | $v_3 = 60.70$ |
| $r_4 = 989.0000$ | | | |
| | $d_4 = 1.0000$ | | |
| $r_5 = \infty$ (auto-iris device 38) | | | |
| | $d_5 = 1.0000$ | | |
| $r_6 = 6.6070$ | | | |
| | $d_6 = 3.0000$ | $n_6 = 1.72916$ | $v_6 = 54.68$ |
| $r_7 = \infty$ | | | |
| | $d_7 = 2.0000$ | | |
| $r_8 = -9.8470$ | | | |
| | $d_8 = 2.0000$ | $n_8 = 1.75520$ | $v_8 = 27.51$ |
| $r_9 = 4.9200$ | | | |
| | $d_9 = 1.7000$ | | |
| $r_{10} = 10.1010$ | | | |
| | $d_{10} = 3.0000$ | $n_{10} = 1.76200$ | $v_{10} = 40.10$ |
| $r_{11} = -14.1680$ | | | |
| | $d_{11} = 2.3300$ | | |
| $r_{12} = \infty$ | | | |
| | $d_{12} = 3.0800$ | $n_{12} = 1.54814$ | $v_{12} = 45.78$ |
| $r_{13} = \infty$ | | | |
| | $d_{13} = 0.0500$ | | |
| $r_{14} = \infty$ | | | |
| | $d_{14} = 1.6000$ | $n_{14} = 1.51400$ | $v_{14} = 74.00$ |
| $r_{15} = \infty$ | | | |
| | $d_{15} = 3.0000$ | | |
| $r_{16} = \infty$ | | | |
| | $d_{16} = 0.7500$ | $n_{16} = 1.51633$ | $v_{16} = 64.15$ |
| $r_{17} = \infty$ | | | |
| | $d_{17} = 0.9600$ | | |
| $r_{18} = \infty$ | | | |

In the apparatus of the eighth embodiment, the object image formed on the Imaging surface of the CCD 16 is brought through the signal cable into the CCU, not shown, and is displayed on the monitor, not shown. In this case, in order to obtain the depth of field an observer requires, the aperture of the auto-iris device is opened or closed in accordance with information from the CCU. The auto-iris device 38 is such that in a range shown in FIGS. 35A–35D, the dimension of its aperture 145 is adjusted. Here, where the aperture 145 of the auto-iris device 38 is stopped down as shown in FIG. 35C or 35D, its dimension is optimized by Eq. (17). However, since the aperture portion of the auto-iris device 38, as shown in the figures, is constructed with several stop plates 146, the aperture may often assume not a round shape, but an abnormal shape. In this case, it is only necessary that the area of the aperture 145 assuming the abnormal shape is converted into that of a circle nearly equal thereto to find the minimum limit value of the aperture diameter of the auto-iris device 38.

However, when the adjustment of the minimum aperture is actually considered at the assembly stage of the auto-iris device, it is difficult to use the above technique as it is. In such a case, the following simple circle-conversion technique can be used. The use of this technique is rather effective in view of the improvement of workability at the assembly stage.

For example, the area of the aperture portion is approximated as an aperture diameter, in terms of the area of a circle inscribed in or circumscribed about a triangle forming the aperture. Specifically, when it is assumed that the minimum aperture of the auto-iris device 38, as shown in FIG. 36, is expressed by an equilateral triangle with a length L of each side and a height H and a circle with a radius R inscribed therein, the following equation is considered:

$$(L \cdot H)/2 \div R^2$$

Here, the radius R becomes $$R = (1/3)H$$
$$= (1/3)\{(\sqrt{3/6})\,L\}$$
$$= (\sqrt{3/6})\,L$$

and the minimum limit value $\phi_2$ of the aperture diameter of the auto-iris device 38, in terms of the circle, can be expressed as $$\phi_2 = 2(\sqrt{3/6})L$$

The minimum aperture shape of the auto-iris device 38 in the eighth embodiment is as shown in FIG. 35C or 35D. FIG. 35C shows the minimum aperture shape found in terms of the area of the circumscribed circle of the aperture shape of the auto-iris device 38, while FIG. 35D illustrates that found in terms of the area of the inscribed circle of the aperture shape. In this case, when the length of each side of the aperture shape shown in FIG. 35C is represented by Lc and the length of each side of the aperture shape in FIG. 35D is represented by Ld, they become $$Lc = 3.11 \text{ (mm)}$$
$$Ld = 1.04 \text{ (mm)}$$

Hence, when the minimum limit value of the aperture diameter of the auto-iris device 38 shown in FIG. 35C is designated by $\phi_2 c$ and the minimum limit value of the aperture diameter of the auto-iris device 38 in FIG. 35D is designated by $\phi_2 d$, they become $$\phi_2 c = 1.8 \text{ (mm)}$$
$$\phi_2 d = 0.6 \text{ (mm)}$$

These values are rough upper and lower values of the minimum limit values of the aperture diameter of the auto-iris device given by Eq. (17).

In the numerical data of the embodiments mentioned above, $r_1, r_2, \ldots$ represent radii of curvature of individual lens surfaces; $d_1, d_2, \ldots$ represent thicknesses of individual lenses or spaces therebetween; $n_1, n_2, \ldots$ represent refractive indices of individual lenses; and $v_1, v_2, \ldots$ represent Abbe's numbers of individual lenses. Also, the object distance and magnification are values relative to the optical system including the eyepiece 4 of the endoscope.

What is claimed is:

1. An imaging apparatus for endoscopes, comprising:
   an endoscope having an observation optical system, said endoscope relaying an object image through said observation optical system, wherein said observation optical system includes an objective lens for forming the object image, a relay optical system for relaying the object image formed by said objective lens as a final image, and an eyepiece for allowing the final image to be observed by an observer's eye; and
   a TV camera removably mounted to said endoscope, said TV camera including a substantially cylindrical housing that contains therein an imaging optical system for re-forming the final image relayed by said endoscope, a stop unit, and an image sensor held by a holder member, said TV camera being provided with a glass cover that is arranged on a light-incident end thereof to form an entrance window and is constructed to be watertight, said stop unit including a stop blade section, said stop blade section being disposed in said imaging optical system and forming a stop whose aperture size is variable, a portion of said stop unit exclusive of said stop blade section being shaped as a cylinder, said stop unit and lenses that are included in said imaging optical system and that are disconnected from said image sensor are immovable along the optical axis so as to be fixedly positioned relative to one another on the optical axis, at least a part of said lenses of said imaging optical system disconnected from said image sensor being supported by an inside face of said cylinder, wherein said image sensor is movable along the optical axis, and said holder member being provided with an adjusting member passing through and projecting from said substantially cylindrical housing so that said image sensor is movable by operating said adjusting member, to change a distance between said lenses of said imaging optical system that are disconnected from said image sensor and said image sensor in a direction of the optical axis for a focusing operation.

2. An imaging apparatus for endoscopes according to claim 1, wherein said relay optical system includes a relay lens system constructed and arranged to relay the object image formed by said objective lens through a series of image formations.

3. An imaging apparatus for endoscopes according to claim 1, wherein said endoscope is replaceable with different endoscopes to be mounted to said TV camera, and said image sensor is constructed to be movable along the optical axis in a step made once every $f'^2/1000$, where f' is a focal length of said imaging optical system, so as to compensate a variation of in-focus position among the endoscopes used with said TV camera.

4. An imaging apparatus for endoscopes according to claim 1, wherein a minimum limit value $\phi_2$ of an aperture diameter of said stop unit satisfies the following condition:

$$1.5\times10^{-4}F/Px \leq \phi_2 \leq 7.32\times10^{-3}[Px/F]Px/F$$

where F is a focal length of an optical system located behind said stop unit and Px is a pixel pitch in a horizontal direction of said image sensor.

5. An imaging apparatus for endoscopes comprising:

an endoscope having an observation optical system, said endoscope relaying an object image through said observation optical system, wherein said observation optical system includes an objective lens for forming the object image, a relay optical system for relaying the object image formed by said objective lens as a final image, and an eyepiece for allowing the final image to be observed by an observer's eye;

a TV photographic adapter having a watertight structure and being removably mounted to said endoscope, said TV photographic adapter comprising an imaging optical system for re-forming the final image relayed by said endoscope, a stop unit, and glass covers that are arranged on a light-incident end and a light-emergent end thereof to form entrance and exit windows and are constructed in such a manner to obtain the watertight structure of said TV photographic adapter, said stop unit including a stop blade section which forms a stop whose aperture size is variable, a portion of said stop unit exclusive of said stop blade section being shaped as a cylinder, at least a pair of lenses of said imaging optical system being supported by an inside face of said cylinder so that said stop unit and at least one lens of said lenses constituting said imaging optical system are fixedly positioned relative to one another on an optical axis; and a TV camera head having a watertight structure and being removably mounted to said TV photographic adapter, said TV camera head comprising an image sensor, and a glass cover that is arranged on a light-incident end thereof to form an entrance window and is constructed in such a manner to obtain the watertight structure of said TV camera head, said TV camera head being constructed to be movable along the optical axis while said TV photographic adapter is fixed to said endoscope, thereby a distance between said at least one lens and said image sensor being changeable along the optical axis for allowing an auto focusing operation to be performed, and wherein said stop unit and said lenses that are included in said imaging optical system that are disconnected from said image sensor are immovable along the optical axis so as to be fixedly positioned with respect to one another on the optical axis.

6. An imaging apparatus for endoscopes according to claim 5, wherein said glass covers of said TV photographic adapter and said TV camera head are made of crystal glass.

* * * * *

UNITED STATES PATENT AND TRADEMARK OFFICE
CERTIFICATE OF CORRECTION

PATENT NO. : 6,069,651
DATED : May 30, 2000
INVENTOR(S) : Tsuyuki et al.

It is certified that error appears in the above-identified patent and that said Letters Patent is hereby corrected as shown below:

Column 31, claim 4,
Line 40, change "$1.5 \times 10^{-4} F/Px \leq \Phi_2 \leq 7.32 \times 10^{-3} [Px/F]\ Px/F$" to
-- $1.5 \times 10^{-4} F/Px \leq \Phi_2 \leq 7.32 \times 10^{-3}\ Px/F$ --

Signed and Sealed this

Twenty-fifth Day of December, 2001

Attest:

JAMES E. ROGAN
*Attesting Officer*     *Director of the United States Patent and Trademark Office*